United States Patent [19]
Kleemann et al.

[11] Patent Number: 6,057,322
[45] Date of Patent: May 2, 2000

[54] BASICALLY-SUBSTITUTED BENZOYLGUANIDINES, A PROCESS FOR PREPARING THEM, THEIR USE AS A MEDICAMENT OR DIAGNOSTIC AGENT, AND A MEDICAMENT CONTAINING THEM

[75] Inventors: Heinz-Werner Kleemann, Bischofsheim; Hans-Jochen Lang, Hofheim; Jan-Robert Schwark, Frankfurt; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 08/903,438

[22] Filed: Jul. 30, 1997

Related U.S. Application Data

[63] Continuation-in-part of application No. 08/592,699, Jan. 21, 1996, abandoned.

[30] Foreign Application Priority Data

Jan. 30, 1995 [DE] Germany .......................... 195 02 795
Feb. 14, 1995 [DE] Germany .......................... 195 04 805

[51] Int. Cl.⁷ ........................ A61K 31/18; A61K 31/165; A61K 31/47; A61K 31/445
[52] U.S. Cl. ........................ 514/255; 514/238.2; 514/312; 514/331; 514/351; 514/392; 514/398; 514/428; 514/399; 514/607; 514/616; 514/618; 514/620; 514/821; 514/866; 514/921; 544/160; 544/400; 544/502; 546/136; 546/157; 546/231; 546/300; 548/306.4; 548/341.5; 548/346.1; 548/566; 564/86; 564/101; 564/133; 564/134; 564/139; 564/142; 564/162; 564/154; 564/165
[58] Field of Search ........................ 544/160, 400, 544/502; 546/136, 157, 231, 300; 548/306.4, 341.5, 346.1, 566; 564/86, 101, 133, 134, 139, 142, 162, 154, 165; 514/238.2, 255, 312, 331, 351, 392, 398, 428, 399, 607, 616, 618, 620, 821, 866, 921

[56] References Cited

U.S. PATENT DOCUMENTS

3,780,027 12/1973 Cragoe, Jr. et al. .................. 260/299.6
5,091,394  2/1992 Englert et al. ........................... 514/331

FOREIGN PATENT DOCUMENTS

| 668265 | 8/1994 | Australia . |
| 589 336 | 3/1994 | European Pat. Off. . |
| 602 523 | 6/1994 | European Pat. Off. . |
| 604 852 | 7/1994 | European Pat. Off. . |
| 43 25 822 | 2/1995 | Germany . |
| WO 94/26709 | 11/1994 | WIPO . |

OTHER PUBLICATIONS

Duff et al., "Amiloride Antiarrhytmic and Electrophysiologic Actions in Patients With Inducible Sustained Ventricular Tachycardia", Circulation, 79(6): 1257–1263 (1989).

Schomig et al., "Inhibition of Na$^{30/H}$ Exchange Suppresses Noradrenaline Release and Arrhythmias In The Ischemic Rat Heart", Eur. Heart J., 9 (suppl. 1): 167 (1988) Book of Abstracts.

*Primary Examiner*—Peter O'Sullivan
*Attorney, Agent, or Firm*—Finnegan, Henderson, Farabow, Garrett & Dunner, L.L.P.

[57] ABSTRACT

Compounds of the formula I

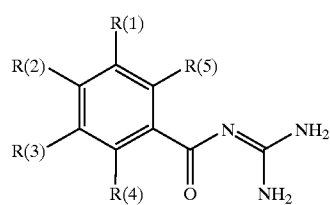

and the pharmaceutically tolerated salts thereof, are described. A process for their preparation and their use as medicaments in cardiovascular diseases are also described.

21 Claims, No Drawings

BASICALLY-SUBSTITUTED BENZOYLGUANIDINES, A PROCESS FOR PREPARING THEM, THEIR USE AS A MEDICAMENT OR DIAGNOSTIC AGENT, AND A MEDICAMENT CONTAINING THEM

This application is a continuation-in-part of U.S. patent application Ser. No. 08/592,699 filed on Jan. 21, 1996, now abandoned, the entire contents of which are expressly incorporated herein by reference.

DESCRIPTION

This invention relates to basically-substituted benzoylguanidines, a process for preparing them, their use as a medicament or diagnostic agent, and a medicament containing them.

The invention relates to benzoylguanidines of the formula (I)

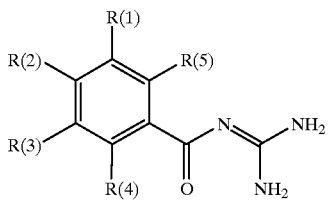

in which:
one of the three substituents R(1), R(2) and R(3) is
R(6)—A—B—D;
R(6) is a basic protonatable radical, i.e. an amino group —NR(7)R(8), an amidino group R(7)R(8)N—C[=N—R(9)]— or a guanidino group

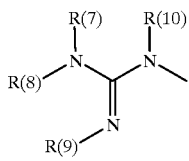

R(7), R(8), R(9) and R(10) are, independently of each other, hydrogen or alkyl having 1, 2, 3 or 4 carbon atoms; or
R(7) and R(8) are,
together, $C_aH_{2a}$;
a is 4, 5, 6 or 7;
wherein, when a=5, 6 or 7, a methylene group of the group $C_aH_{2a}$ can be replaced by a heteroatom group O, $SO_m$ or NR(11), or
R(8) and R(9) or R(9) and R(10) or R(7) and R(10) are a group $C_aH_{2a}$;
a is 2,3,4 or 5;
where, when a=3, 4 or 5, a methylene group of the group $C_aH_{2a}$ can be replaced by a heteroatom group, O, $SO_m$ or NR(11);
m is zero, 1 or 2;
R(11) is hydrogen or methyl; or
R(6) is a basic heteroaromatic ring system having 1–9 carbon atoms;
A is $C_bH_{2b}$;
b is 1, 2, 3, 4, 5, 6, 7, 8, 9 or 10;
where, in the group $C_bH_{2b}$, one or two methylene groups can be replaced by one of the groupings selected from the group consisting of —O—, —CO—, —CH[OR(20)]—, $—SO_m—$, —NR(20)—, —NR(20)—CO—, —N(20)—CO—NH—, —NR(20)—CO—NH—$SO_2$—

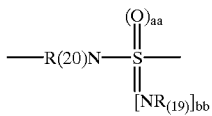

and $—SO_{aa}\{NR(19)\}_{bb}—$;
and where, in the group $C_bH_{2b}$, a methylene group can be replaced by —CH—R(99), where R(99), together with R(7), forms a pyrrolidine or piperidine ring;
aa is 1 or 2;
bb is 0 or 1;
aa+bb=2;
R(19) is hydrogen or alkyl having 1, 2, 3 or 4 carbon atoms
R(20) is hydrogen or methyl;
B is a phenylene or naphthylene radical

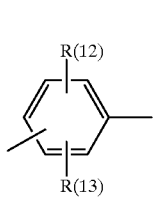 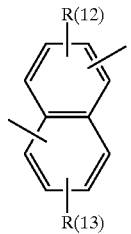

R(12) and R(13) are,
independently of each other, hydrogen, methyl, F, Cl, Br, I, $CF_3$ or $—SO_w—R(14)$;
R(14) is methyl or NR(15) R(16);
R(15) and R(16) are,
independently of each other, hydrogen or alkyl having 1, 2, 3 or 4 carbon atoms;
w is zero, 1 or 2;
D is $—C_dH_{2d}—X_f—$;
d is zero, 1, 2, 3 or 4;
X is —O—, —CO—, $—CH\{OR(21)\}—$, $—SO_m—$ or —NR(21)—;
f is zero or 1;
R(21) is hydrogen or methyl;
m is zero, 1 or 2;
and in each case the other two of the substituents R(1) and R(2) and R(3) are,
independently of each other, hydrogen, F, Cl, Br, I, —CN, $—(C_1-C_8)$-alkyl, $—(C_2-C_8)$-alkenyl, —NR(35)R(36) or R(17)—$C_gH_{2g}$—$Z_h$—;
g is zero, 1, 2, 3 or 4;
h is zero or 1;
R(35) and R(36) are,
independently of each other, hydrogen or alkyl having 1, 2, 3, 4, 5 or 6 carbon atoms; or
R(35) and R(36) are,
together, 4–7 methylene groups of which one $CH_2$ group can be replaced by oxygen, —S—, —NH—, $—NCH_3$ or —N—benzyl;
Z is —O—, CO—, $—SO_v—$, —NR(18)—, —NR(18)—CO—, —NR(18)—CO—NH— or —NR(18)—$SO_2$—;

R(18) is hydrogen or methyl;
v is zero, 1 or 2;
R(17) is hydrogen, cycloalkyl having 3, 5 or 6 carbon atoms, or $C_kF_{2k+1}$—;
k is 1, 2 or 3, or
R(17) is pyrrol-1-yl, pyrrol-2-yl or pyrrol-3-yl,
which is not substituted or is substituted by 1–4 substituents selected from the group consisting of F, Cl, Br, I, —CN, $(C_2-C_8)$-alkanoyl, $(C_2-C_8)$-alkoxy-carbonyl, formyl, carboxyl, —$CF_3$, methyl and methoxy; or
R(17) is —$(C_3-C_8)$-cycloalkyl or phenyl,
which is not substituted or is substituted by 1–3 substituents selected from the group consisting of F and Cl, —$CF_3$, methyl, hydroxyl, methoxy, —NR(37)R(38), $CH_3SO_2$— and $H_2NO_2S$—;
R(37) and R(38) are
hydrogen or —$CH_3$;
R(4) and R(5) are,
independently of each other, hydrogen, alkyl having 1, 2, 3 or 4 carbon atoms, F, Cl, —OR(32), —NR(33)R(34) or —$C_rF_{2r+1}$;
R(32), R(33) and R(34) are,
independently of each other, hydrogen or alkyl having 1, 2 or 3 carbon atoms;
r is 1, 2, 3 or 4;
and the pharmacologically tolerated salts thereof.
Compounds of the formula I are preferred in which:
R(1) is hydrogen, F, Cl, —$(C_1-C_4)$-alkyl, —$(C_2-C_4)$-alkenyl,
—NR(35)R(36) or R(17) —$C_gH_{2g}$—$Z_h$—;
R(35) and R(36) are,
independently of each other, hydrogen, methyl or ethyl; or
R(35) and R(36) are,
together, 4–5 methylene groups of which one $CH_2$ group can be replaced by oxygen, —S—, —NH— or —$NCH_3$;
R(17) is hydrogen, cycloalkyl having 5 or 6 carbon atoms, or $C_kF_{2k+1}$;
k is 1, 2 or 3,
g is zero, 1, 2, 3 or 4;
h is zero or 1;
Z is —O—, —CO—, —$SO_v$—, —NR(18)—, —NR(18)—CO—, —NR(18)—CO—NH— or —NR(18)—$SO_2$—;
R(18) is hydrogen or methyl;
v is zero, 1 or 2;
or, if g and h are zero,
R(17) is pyrrol-1-yl, pyrrol-2-yl or pyrrol-3-yl,
which is not substituted or is substituted by 1–2 substituents selected from the group consisting of F, Cl, $(C_2-C_5)$-alkanoyl, $(C_2-C_5)$-alkoxycarbonyl, formyl, carboxyl, —$CF_3$, methyl and methoxy; or
R(17) is —$(C_3-C_8)$-cycloalkyl or phenyl,
which is not substituted or is substituted by 1–2 substituents selected from the group consisting of F and Cl, —$CF_3$, methyl, methoxy, —NR(37)R(38), $CH_3SO_2$— and $H_2NO_2S$—;
R(37) and R(38) are,
independently of each other, hydrogen or —$CH_3$;
one of the substituents R(2) and R(3) is R(6)—A—B—D;
R(6) is —NR(7)R(8), an amidino group R(7)R(8)N—C[=N—R(9)]— or a guanidino group

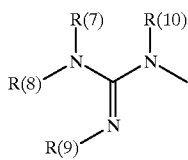

R(7), R(8), R(9) and R(10) are independently of each other, hydrogen or alkyl having 1, 2, 3 or 4 carbon atoms; or
R(7) and R(8) are,
together, $C_aH_{2a}$;
a is 4, 5, 6 or 7;
where, when a=5, 6 or 7, a methylene group of the group $C_aH_{2a}$ can be replaced by a heteroatom group O, $SO_m$ or NR(11);
R(11) is hydrogen or methyl; or
R(8) and R(9) are,
together, $C_aCH_{2a}$;
a is 2, 3, 4 or 5;
where, when a=3, 4 or 5, a methylene group of the group $C_aH_{2a}$ can be replaced by a heteroatom group O, $SO_m$ or NR(11);
m is zero, 1 or 2; or
R(6) is imidazolyl, pyridyl, quinolinyl or isoquinolinyl;
A is $C_bH_{2b}$;
b is 1, 2, 3, 4 or 5,
where, in the group $C_bH_{2b}$, one or two methylene groups can be replaced by one of the groupings selected from the group consisting of —O—, —CO—, —CH[OR(20)]—, —$SO_m$—, NR(20), —NR(20)—CO—, —NR(20)—CO—NH—, —NR(20)—CO—NH—$SO_2$—,

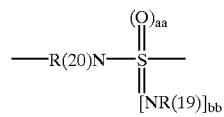

and —$SO_{aa}${NR(19)}$_{bb}$—;
and where, in the group $C_bH_{2b}$, a methylene group can be replaced by —CH—R(99), where R(99), together with R(7), forms a pyrrolidine or piperidine ring;
aa is 1 or 2;
bb is 0 or 1;
aa+bb=2;
R(19) is hydrogen or alkyl having 1, 2, 3 or 4 carbon atoms;
R(20) is hydrogen or methyl;
B is a phenylene or naphthylene radical

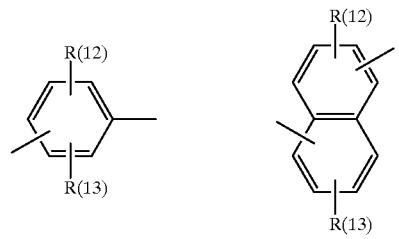

R(12) and R(13) are,
independently of each other, hydrogen, methyl, F, Cl, $CF_3$, or —$SO_2$—R(14);

R(14) is methyl or NR(15)R(16);
R(15) and R(16) are,
independently of each other, hydrogen or alkyl having 1, 2, 3 or 4 carbon atoms;
D is —$C_dH_{2d}$—$X_f$—;
d is zero, 1, 2, 3 or 4;
X is —O—, —CO—, —CH[OR(21)]—, —$SO_m$— or —NR(21)—;
f is zero or 1;
R(21) is hydrogen or methyl;
m is zero, 1 or 2;
and in each case the other of the radicals R(2) and R(3) is hydrogen, alkyl having 1, 2, 3 or 4 carbon atoms, F, Cl or $CF_3$;
R(4) and R(5) are,
independently of each other, hydrogen, alkyl having 1, 2, or 3 carbon atoms, F, Cl or —$CF_3$;
and the pharmacologically tolerated salts thereof.

Compounds of the formula I are particularly preferred in which:
R(1) is hydrogen, F, Cl, alkyl having 1, 2, 3 or 4 carbon atoms, —NR(35)R(36) or R(17)—$C_gH_{2g}$—$Z_h$—;
g is zero, 1, 2, 3 or 4;
h is zero or 1;
Z is —O—, —CO—, —$SO_v$—, —NR(18)—, —NR(18)—CO—, —NR(18)—CO—NH— or —NR(18)—$SO_2$—;
R(18) is hydrogen or methyl;
v is zero, 1 or 2;
R(17) is hydrogen, cycloalkyl having 5 or 6 carbon atoms, or $CF_3$—; or, if g and h are zero,
R(17) is pyrrol-1-yl,
which is not substituted or is substituted by 1–2 substituents selected from the group consisting of F, Cl, ($C_2$-$C_5$)-alkanoyl, ($C_2$-$C_5$)-alkoxycarbonyl, —$CF_3$ and methyl; or
R(17) is —($C_5$-$C_6$)-cycloalkyl or phenyl,
which is not substituted or is substituted by a substituent which is selected from the group consisting of F and Cl, —$CF_3$, methyl, $CH_3SO_2$— and $H_2NO_2S$—;
R(35) and R(36) are,
independently of each other, hydrogen, methyl or ethyl; or
R(35) and R(36) are,
together, 4–5 methylene groups of which one $CH_2$ group can be replaced by oxygen, —S—, —NH— or —$NCH_3$;
one of the substituents R(2) and R(3) is
R(6)—A—B—D—;
R(6) is —NR(7)R(8), an amidino group R(7)R(8)N—C[=N—R(9)]— or a guanidino group

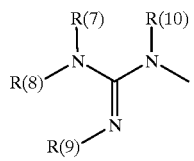

R(7) is
hydrogen or alkyl having 1, 2, 3 or 4 carbon atoms;
R(8), R(9) and R(10) are,
independently of each other, hydrogen, methyl or ethyl; or
R(7) and R(8) are, together, $C_aH_{2a}$;
a is 4 or 5;
where, when a=5, a methylene group of the group $C_aH_{2a}$ can be replaced by NR(11),
R(11) is a hydrogen or methyl; or
R(6) is imidazolyl or pyridyl;
A is $C_bH_{2b}$;
b is 1, 2, 3, 4 or 5,
where, in the group $C_bH_{2b}$, one or two methylene groups can be replaced by one of the groupings selected from the group consisting of —CO—, —CH[OR(20)]—, —NR(20)—CO—,

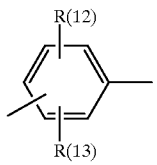

—$SO_{aa}$[NR(19)]$_{bb}$ and —$SO_2$—;
and where, in the group $C_{2b}H_{2b}$, a methylene group can be replaced by —CH—R(99), where R(99), together with R(7), forms a pyrrolidine or piperidine ring;
aa is 1 or 2;
bb is 0 or 1;
aa+bb=2;
R(19) is hydrogen or alkyl having 1, 2, 3 or 4 carbon atoms;
R(20) is hydrogen or methyl;
or, if b is 2, 3, 4 or 5,
a carbon atom in $C_bH_{2b}$ can be replaced by a grouping —O—, —S—, —NR(20)—, —NR(20)—CO— or —NR(20)—CO—NH—;
B is a phenylene radical,

R(12)
R(13)

R(12) and R(13) are,
independently of each other, hydrogen, methyl, F, Cl, $CF_3$ or —$SO_2R(14)$;
R(14) is methyl or $NH_2$;
D is —$CH_2$—, —O—, —CO—, —$SO_m$— or —NR(21)—;
m is zero or 2;
R(21) is hydrogen or methyl;
and in each case the other of the radicals R(2) and R(3) is hydrogen;
R(4) and R(5) are,
independently of each other, hydrogen, alkyl having 1, 2 or 3 carbon atoms, F, Cl or —$CF_3$;
and the pharmaceutically tolerated salts thereof.

Compounds of the formula I are very particularly preferred in which
R(1) is hydrogen, F, Cl, alkyl having 1, 2, 3 or 4 carbon atoms, —NR(35)R(36) or R(17)—$C_gH_{2g}$—$Z_h$—;
g is zero or 1;
h is zero or 1;
Z is —O—, —CO—, —NR(18)—CO—, —NR(18)—CO—NH— or —NR(18) —$SO_2$—;
R(18) is hydrogen or methyl;

or, if g is 1;

Z is —SO$_2$—;

R(17) is hydrogen or CF$_3$—;

R(35) and R(36) are,
  independently of each other, hydrogen, methyl or ethyl;
  or R(35) and R(36) are,
  together, 4–5 methylene groups of which one CH$_2$ group can be replaced by oxygen, —S—, —NH— or —NCH$_3$;

one of the substituents R(2) and R(3) is

R(6)—A—B—O;

R(6) is —NR(7)R(8) or a guanidino group

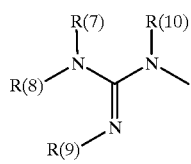

R(7) is
  hydrogen or alkyl having 1, 2, 3 or 4 carbon atoms;

R(8), R(9) and R(10) are,
  independently of each other, hydrogen, methyl or ethyl;
  or R(7) and R(8) are,
  together, C$_a$H$_{2a}$;
  a is 4 or 5;
    where, when a=5, a methylene group of the group C$_a$H$_{2a}$ can be replaced by —NH— or —NCH$_3$—,
  or R(6) is imidazolyl;

A is C$_b$H$_{2b}$;
  b is 1, 2, 3 or 4;
    where, in the group C$_b$H$_{2b}$, one or two methylene groups can be replaced by one of the groupings selected from the group consisting of —CO—,

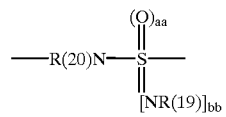

—SO$_{aa}$[NR(19)]$_{bb}$— and —SO$_2$—, and where, in the group C$_b$H$_{2b}$, a methylene group can be replaced by —CH—R(99), where R(99), together with R(7), can form a pyrrolidine or piperidine ring;
or, if b is 2, 3 or 4,
a methylene group in the group C$_b$H$_{2b}$ can be replaced by a grouping —O— or —S—;

aa is 1 or 2;
bb is 0 or 1;
aa+bb=2;
R(19) is hydrogen or alkyl having 1, 2, 3 or 4 carbon atoms
R(20) is hydrogen or methyl;

B is a phenylene radical,

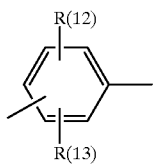

R(12) and R(13) are,
  hydrogen;
and in each case the other of the radicals R(2) and R(3) is
  hydrogen;
R(4) and R(5) are
  hydrogen;
and the pharmacologically tolerated salts thereof.

Particular preference is given to a compound which is selected from the group consisting of 4-[4-N-(dimethylaminoethyl)methylsulfamoyl]phenoxy-3-trifluoromethylbenzoylguanidine dihydrochloride; 4-[4-(4-methylpiperazinosulfonyl)phenoxy]-3-trifluoromethylbenzoylguanidine dihydrochloride; 4-[4-(2-pyrrolidineethylaminosulfonyl)phenoxy]-3-trifluoromethylbenzoylguanidine dimaleate; 4-[4-(2-piperidineethylaminosulfonyl)phenoxy]-3-trifluoromethylbenzoylguanidine dimaleate; 4-[4-(N-dimethylamino-n-propyl)sulfamoyl]phenoxy-3-trifluoromethylbenzoylguanidine; 4-[4-(N-dimethylaminoethyl)sulfamoyl]phenoxy-3-trifluoromethylbenzoylguanidine; 4-[4-imidosulfamoyl)phenoxy-3-trifluoromethylbenzoyl-guanidine; 3-trifluoromethyl-4-(4-N-methylimidosulfamoyl)-phenoxybenzoylguanidine; 3-methyl-4-(4-(1-methylpiperazin-4-ylsulfonyl)phenoxy)-benzoylguanidine; 4-(4-guanidinosulfonyl)phenoxy-3-trifluoromethylbenzoyl-guanidine; 4-[4-(2-imidazolylthioacetyl)phenoxy]-3-methylsulfonyl-benzoylguanidine dihydrochloride; 4-[4-(N,N'-dimethyl-S-iosthiuronylacetyl)phenoxy]-3-methylsulfonylbenzoylguanidine dihydrochloride; 4-[4-(2-benzimidazolylthioacetyl)phenoxy]-3-methyl-sulfonylbenzoylguanidine dihydrochloride; 4-[4-(2-N-imidazolyl-1-hydroxyethyl)phenoxy]-3-methyl-sulfonylbenzoylguanidine dihydrochloride; 4-[4-(N,N-dimethylglycylamino)phenoxy]-3-methylsulfonyl-benzoylguanidine dihydrochloride; 4-[4-(N,N-diethylaminoethyl)aminosulfonylphenoxy]-3-methylsulfonylbenzoylguanidine dihydrochloride; 4-[4-(4-imidazolylethyl)aminosulfonylphenoxy]-3-methyl-sulfonylbenzoylguanidine dihydrochloride; 4-[4-(3-N-imidazolyl-1-propyl)aminosulfonylphenoxy]-3-methylsulfonylbenzoylguanidine dihydrochloride; 4-[4-(1-methyl-2-pyrrolidinylethyl)aminosulfonylphenoxy]-3-methylsulfonylbenzoylguanidine dihydrochloride; 4-[4-(N-piperidinoethyl)aminosulfonylphenoxy]-3-methyl-sulfonylbenzoylguanidine dihydrochloride; 4-[4-(2-dimethylaminoethyl)sulfonylmethylphenoxy]-3-methylsulfonylbenzoylguanidine dihydrochloride; 4-[4-(2-dimethylaminoethyl)sulfonylmethylphenoxy]-3-trifluoromethylbenzoylguanidine dihydrochloride.

The indicated alkyl radicals can be either straight-chain or branched.

A basic heteroaromatic ring system having 1–9 carbon atoms was understood to mean, in particular, radicals which are derived from cyclopentyl, phenyl or naphthyl and in which one or more CH groups is/are replaced by N. Heteroaryl was, in particular, imidazolyl, pyrazolyl, oxazolyl, isoxazolyl, thiazolyl, isothiazolyl, pyridyl, quinolyl and isoquinolyl. Halogen was F, Cl, Br or I.

If the compounds of the formula I contain centers of asymmetry, formula I describes both the individual optical antipodes and also their possible enantiomeric mixtures.

The invention furthermore relates to a process for preparing a compound I, which comprises reacting a compound of the formula II

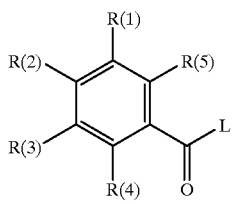

in which R(1) to R(5) have the given meaning and L is a leaving group which can readily be substituted nucleophilically, with guanidine, and, where appropriate, converting the product into a pharmacologically tolerated salt.

The activated acid derivatives of the formula II, in which L is an alkoxy, preferably a methoxy group, a phenoxy group, phenylthio, methylthio, or a 3-pyridyloxy or 2-pyridyltyhio group, or a nitrogen heterocycle, preferably 1-imidazolyl, are advantageously obtained, in a known manner, from the underlying carbonyl chlorides (formula II, L=Cl), which, for their part, can in turn be prepared, in a known manner, from the underlying carboxylic acids (formula II, L=OH), for example using thionyl chloride.

In addition to the carbonyl chlorides of the formula II (L=Cl), other activated acid derivatives of the formula II can also be prepared, in a known manner, directly from the underlying benzoic acid derivatives (formula II, L=OH), for example the methyl esters of the formula II where L=OCH$_3$ by treatment with gaseous HCl in methanol, the imidazolides of the formula II by treatment with carbonyl diimidazole [L=1-imidazole, Staab, Angew. Chem. Int. Ed. Engl. 1, 351–367 (1962)], the mixed anhydrides 11 using ClCOOC$_2$H$_5$ or tosyl chloride in the presence of triethylamine in an inert solvent, and benzoic acids can also be activated with dicyclohexyl-carbodiimide (DCC) or with O[(cyano(ethoxycarbonyl)-methylene)amino]-1,1,3,3-tetramethyluronium tetrafluoroborate ("TOTU") [Proceedings of the 21. European Peptide Symposium, Peptides 1990, Editors E. Giralt and D. Andreu, Escom, Leiden, 1991]. A series of suitable methods for preparing activated carboxylic acid derivatives of the formula II can be found in J. March, Advanced Organic Chemistry, Third Edition (John Wiley & Sons, 1985), p. 350, where the source references are cited.

An activated carboxylic acid derivative of the formula II is reacted with guanidine, in a known manner, in a protic or aprotic polar, but inert, organic solvent. Methanol, isopropanol or THF have proved to be of value in the reaction of the methyl benzoate (II, L=OME) with guanidine at temperatures of from 20° C. to the boiling point of the solvents. Most reactions of compounds II with salt-free guanidine were advantageously carried out in aprotic inert solvents such as THF, dimethoxyethane, dioxane or isopropanol. However, water can also be employed as a solvent in the reaction of II and guanidine when a base is used.

If L=Cl, the reaction is advantageously carried out with the addition of an acid-capturing agent, for example in the form of excess guanidine, in order to bind the hydrohalic acid.

Some of the underlying benzoic acid derivatives are known. They are prepared, using methods which are known from the literature, by, for example, converting the finished radical R(6)—A—B—C$_d$H$_{2d}$—X$_f$—, or a precursor thereof, by halogen exchange, into a benzoic acid derivative of the formula III

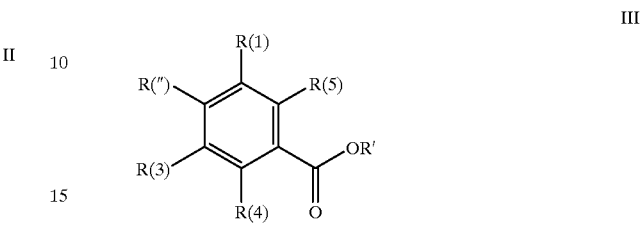

in which the substituent R' has the meaning of a lower alkyl radical, for example methyl or ethyl, and R" is halogen. The reactions are described in the literature, for example as a nucleophilic substitution reaction, as a free-radical Ullmann reaction or as palladium-catalyzed reactions.

The introduction of the benzenesulfonamide derivatives which are substituted in the phenyl moiety by sulfur, oxygen or nitrogen nucleophiles is achieved using methods, which are known from the literature, of nucleophilic substitution on the aromatic moiety. Halides and trifluoromethanesulfonates have proved to be of value, in this substitution, as leaving group on the benzoic acid derivative. The reaction is advantageously carried out in a dipolar aprotic solvent, such as DMF or TMU, at a temperature of from 0° C. to the boiling point of the solvent, preferably from 80° C. to the boiling point of the solvent. An alkali metal salt or alkaline earth metal salt possessing an anion of high basicity and low nucleophilicity, for example K$_2$CO$_3$ or CsCO$_3$, advantageously serves as acid-capturing agent.

Most of the R(6)—A—B—C$_d$H$_{2d}$—X$_f$— compounds used as precursors are known and some of them are also commercially available as reagents. They are prepared by methods which are known from the literature and with which the person skilled in the art is familiar.

Some substituents can successfully be introduced into the 4 and 5 positions by methods which are known from the literature, namely palladium-mediated cross-coupling of aryl halides with, for example, organostannanes, organoboronic acids or organoboranes or organocopper or organozinc compounds.

In general, benzoylguanidines I are weak bases and can bind acid with the formation of salts. Suitable acid addition salts are salts of all pharmacologically acceptable acids, for example halides, in particular hydrochlorides, lactates, sulfates, citrates, tartrates, ascorbates, acetates, phosphates, methylsulfonates and p-toluenesulfonates.

The compounds I are substituted acylguanidines.

The best known representative of the acylguanidines is the pyrazine derivative amiloride, which is used in therapy as a potassium-sparing diuretic. A large number of other amiloride-type compounds are described in the literature, for example dimethylamiloride or ethylisopropylamiloride.

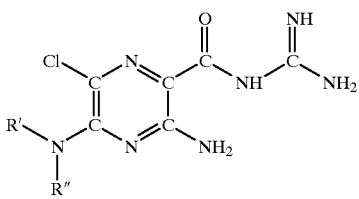

Amiloride: R', R"=H
Dimethylamiloride: R',R"=CH$_3$
Ethylisopropylamiloride: R'=C$_2$H$_5$, and R"=CH(CH$_3$)$_2$ Moreover, tests are known which suggest that amiloride has antiarrhythmic properties (Circulation 79, 1257 to 1263 (1989)). However, militating against its widespread use as an antiarrhythmic is the fact that this effect is only weakly expressed and is accompanied by hypotensive and saluretic activity, and these side-effects are undesirable in the treatment of disturbances of cardiac rhythm. Experiments on isolated animal hearts have also suggested that amiloride has antiarrhythmic properties (Eur. Heart J. 9 (suppl. 1): 167 (1988) (book of abstracts)).

Thus, it has been found that artificially induced ventricular fibrillation in rat hearts can be completely suppressed by amiloride. In this model, the abovementioned amiloride derivative ethylisopropylamiloride was even more potent than amiloride itself.

U.S. Pat. No. 5,091,394 (HOE 89/F 288) describes benzoylguanidines which carry only a hydrogen atom in the position corresponding to the radical R(1) and in which none of the substituents has the meaning of R(5)—A—B—D—. European Laid-Open Application 0 556 674 A (HOE 92/F 034) proposes 3,5-substituted benzoylguanidines in which, however, the substituent R(2) does not have the meaning of R(5)—A—B—D—, which is claimed in accordance with the present invention.

U.S. Pat. No. 3,780,027 claims acylguanidines which are structurally similar to the compounds of the formula I and which are derived from commercially available loop diuretics, such as bumetanide. Accordingly, these compounds are reported to have powerful salidiuretic activity.

It was surprising, therefore, that the novel compounds have no undesirable, disadvantageous salidiuretic properties but, nevertheless, have a very good antiarrhythmic activity against arrhythmias as they occur, for example, in connection with oxygen deficiencies. Due to their pharmacological properties, the compounds are outstandingly suitable for use, as antiarrhythmic pharmaceuticals having a cardioprotective component, for the prophylaxis and treatment of infarction and for the treatment of angina pectoris, in which context they also preventively inhibit, or reduce greatly, the pathophysiological processes associated with the development of ischemically induced damage, in particular when ischemically induced cardiac arrhythmias are triggered. Due to their protective activity against pathological hypoxic and ischemic situations, the novel compounds of the formula I can, owing to inhibition of the cellular Na$^+$/H$^+$ exchange mechanism, be used as pharmaceuticals for treating all acute or chronic damage which is triggered by ischemia or for treating diseases which are directly or colaterally induced thereby. This applies to their use as pharmaceuticals for surgical interventions, for example in connection with organ transplants, where the compounds can be used for the protection of the organs in the donor before and during their removal, for the protection of removed organs, for example during their treatment with, or storage in, physiological bathing fluids, and also during their transfer into the recipient organism. Equally, the compounds are valuable protective pharmaceuticals when angioplastic surgical interventions are carried out, for example on the heart or on peripheral blood vessels. In correspondence with their protective activity against ischemia-induced damage, the compounds are also suitable as pharmaceuticals for the treatment of ischemias of the nervous system, in particular of the central nervous system, where they are suitable, for example, for the treatment of stroke or of brain edema. Moreover, the compounds of the formula I according to the invention are also suitable for the treatment of forms of shock, for example allergic, cardiogenic, hypovolemic and bacterial shock.

Moreover, the compounds of the formula I according to the invention are distinguished by a powerful inhibitory action on cell proliferation, for example fibroblast cell proliferation and proliferation of the smooth vascular muscle cells. This is why the compounds of the formula I are suitable as valuable therapeutic agents for diseases in which cell proliferation is a direct or collateral cause, and they can therefore be used as antiatherosclerotics, agents against diabetic late complications, cancers, fibrotic disorders, such as pulmonary fibrosis, hepatic fibrosis or renal fibrosis, organ hypertrophies and hyperplasias, in particular in prostatic hyperplasia or prostatic hypertrophy.

The compounds according to the invention are valuable inhibitors of the cellular sodium/proton antiporter (Na$^+$/H$^+$ exchanger), which is elevated in a large number of diseases (essential hypertension, atherosclerosis, diabetes and the like) even in those cells which are readily accessible to measurements, such as in erythrocytes, thrombocytes or leucocytes. The compounds according to the invention are therefore suitable as outstanding and simple scientific tools, for example in their use as diagnostics for determining, and distinguishing between, particular forms of hypertension, and also of atherosclerosis, diabetes, proliferative disorders and the like. Moreover, the compounds of the formula I are suitable for preventive therapy for preventing the genesis of hypertension, for example of essential hypertension.

In addition to a strongly inhibitory effect on the Na$^+$/H$^+$ exchanger the solubility in water of the compounds according to the invention is significantly improved in contrast to the known compounds. They are therefore much better suited to intravenous administration.

Pharmaceuticals which contain a compound I can be administered orally, parenterally, intravenously, rectally or by inhaling, the preferred way of administration depending on the particular symptom of the disease. The compounds I can be used by themselves or together with pharmaceutical auxiliaries, and they can be employed both in veterinary medicine and human medicine.

A person skilled in the art knows, on the basis of his expert knowledge, which auxiliaries are suitable for the desired pharmaceutical formulation. Auxiliaries which can be used in addition to solvents, gel formers, bases for suppositories, tableting auxiliaries, and other excipients for active substances are, for example, antioxidants, dispersants, emulsifiers, antifoams, flavor improvers, preservatives, solubilizers or colorants.

For an oral dosage form, the active compounds together with the suitable additives, such as carriers, stabilizers or inert diluents, are mixed and formulated by customary methods to give suitable dosage forms, such as tablets, sugar-coated tablets, hard gelatin capsules, or aqueous, alcoholic or oily solutions. Inert excipients which can be used are, for example, gum arabic, magnesia, magnesium carbonate, potassium phosphate, lactose, glucose or starch, in particular corn starch. Dry granules or moist granules can be used for the preparation. Examples of oily carriers or examples of solvents are vegetable or animal oils, such as sunflower oil or cod liver oil.

For subcutaneous or intravenous administration, the active compounds, if desired together with the substances which are customary for this purpose, such as solubilizers, emulsifiers or other auxiliaries, are dissolved, suspended or emulsified. Examples of suitable solvents are: water, physiological saline solution or alcohols, for example ethanol, propanol, glycerol, and also sugar solutions, such as glucose or mannitol solutions, or else a mixture of the various solvents which have been mentioned above.

Pharmaceutical formulations which are suitable for administration in the form of aerosols or sprays are, for example, solutions, suspensions or emulsions of the active substance of the formula I in a pharmaceutically acceptable solvent, such as, in particular, ethanol or water, or else in a mixture of such solvents.

If required, the formulation can also contain other pharmaceutical auxiliaries, such as surfactants, emulsifiers and stabilizers, and a propellant gas. The concentration of active substance in such a preparation is generally from about 0.1 to 10, in particular from about 0.3 to 3% by weight.

The dose of the active substance of the formula I to be administered and the frequency of administration will depend on the power and duration of action of the compounds used; in addition also on the nature and severity of the disease to be treated and on the sex, age, weight and individual responsiveness of the mammal to be treated.

On average, the daily dosage rate of a compound of the formula I in the case of a patient of approximately 75 kg will be at least 0.001 mg/kg, preferably 0.01 mg/kg, up to not more than 10 mg/kg, preferably 1 mg/kg, of body weight. If the disease is acute, such as immediately after suffering a cardiac infarction, even higher and, in particular, more frequent, doses may be required, for example up to 4 single doses per day. In particular, for intravenous administration, such as in the case of a patient who has suffered an infarction and is under intensive care, up to 200 mg per day may be required.

| AIBN | α,α-azobisisobutyronitrile |
| Bn | benzyl |
| brine | saturated aqueous solution of NaCl |
| $CH_2Cl_2$ | dichloromethane |
| DCI | desorption chemical ionization |
| DIP | diisopropyl ether |
| DMA | dimethylacetamide |
| DME | dimethoxyethane |
| DMF | N,N-dimethylformamide |
| EA | ethyl acetate (EtOAc) |
| EI | electron impact |
| eq | equivalent |
| ES | electrospray ionization |
| Et | ethyl |
| FAB | fast atom bombardment |
| HEP | n-heptane |
| HOAc | acetic acid |
| Me | methyl |
| MeOH | methanol |
| mp | melting point |
| MTB | methyl tert-butyl ether |
| NBS | N-bromosuccinimide |
| NMP | N-methylpyrrolidone |

-continued

| RT | room temperature |
| THF | tetrahydrofuran |
| TMU | N,N,N',N'-tetramethylurea |
| CNS | central nervous system |

Experimental Section
General protocol for preparing benzoylguanidines (I)
Variant A: from benzoic acids (II, L=OH)

0.01 mol of the benzoic acid derivative of the formula II was dissolved or suspended in 60 ml of anhydrous THF and 1.78 g (0.011 mol) of carbonyl diimidazole were then added. After the mixture was stirred at RT for 2 hours, 2.95 g (0.05 mol) of guanidine was introduced into the reaction solution. After the mixture had been stirred overnight, the THF was distilled off under reduced pressure (rotary evaporator), water was added, the pH was adjusted to from 6 to 7 with 2 N HCl and the corresponding benzoylguanidine (formula I) was filtered off. The benzoylguanidines thus obtained can be converted into the corresponding salts by treatment with aqueous, methanolic or ethereal hydrochloric acid or other pharmacologically tolerated acids.

General protocol for preparing benzoylguanidines (I)
Variant B: from alkyl benzoates (II, L=O-alkyl)

5 mmol of the alkylbenzoate of the formula II and 25 mmol of guanidine (free base) was dissolved in 15 ml of isopropanol or suspended in 15 ml of THF and the mixture was boiled under reflux until conversion was complete (monitoring by thin layer chromatography) (typical reaction time, from 2 to 5 h). The solvent was distilled off under reduced pressure (rotary evaporator) and the residue was taken up in 300 ml of EA and this solution was washed 3× with 50 ml of $NaHCO_3$ solution on each occasion. It was dried over $Na_2SO_4$ and the solvent was distilled off in vacuo; the residue was chromatographed on silica gel using a suitable eluent, e.g. EA/MeOH, 5:1. (Salt formation, cf. Variant A)

EXAMPLE 1

4-(4-Aminosulfonyl)phenoxy-3-trifluoromethylbenzoylguanidine

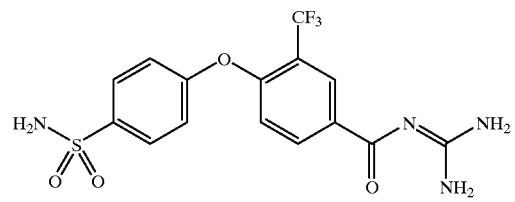

a) Methyl 4-fluoro-3-trifluoromethylbenzoate 5 g of 4-fluoro-3-trifluoromethylbenzoic acid and 9 ml of $SOCl_2$ were stirred at 60° C. for 8 h in 50 ml of MeOH. The volatile constituents were then removed in vacuo and 5.1 g were obtained of a colorless oil which was subjected to further use without purification.

| $R_f$ (EA/MeOH 10:1) = 0.74 | MS (DCI) 223 (M + H)$^+$ | b) Methyl 4-(4-aminosulfonyl)phenoxy-3-trifluoromethylbenzoate 890 mg of fluoride a), 690 mg of 4-hydroxybenzenesulfonamide and 1.1 g of $K_2CO_3$ were stirred at 120° C. for 2 h in 5 ml of DMF. The mixture was allowed to cool to RT, 100 ml of brine were added and the whole was extracted 3× with 50 ml of EA on each occasion. The organic phase was dried over Na$_2$SO$_4$ and the solvent was removed in vacuo. 1.2 g of a colorless oil were obtained.

| R$_f$ (MTB) = 0.45 | MS (DCI) 376 (M + H)$^+$ |
|---|---| c) 4-(4-Aminosulfonyl)phenoxy-3-trifluoromethyl benzoylguanidine 550 mg of methyl ester 1 b) were guanylated in accordance with Variant B. 170 mg of an amorphous powder were obtained.

| R$_f$ (EA/MeOH 10:1) = 0.50 | MS (ES) 403 (M + H)$^+$ |
|---|---| was converted into the hydrochloride.
mp>270° C.

EXAMPLE 2
4-[4-(N-t-Butylimido-N'-t-butyl)sulfamoyl]-3-trifluoromethylbenzoylguanidine dihydrochloride

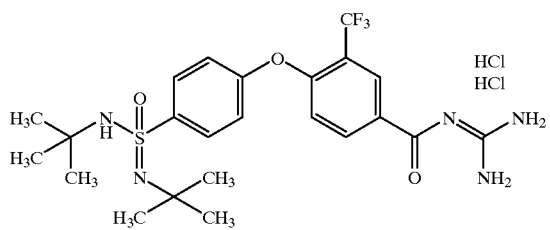

a) 4-Fluorobenzenesulfonic acid N,N'-bis-t-butylimidoamide 10.3 ml of bromine were added to 900 ml of t-butylamine at −30° C. The mixture was allowed to warm to −5° C. and 6.6 ml of 4-fluorothiophenol were added. The mixture was warmed to RT and then stirred at this temperature for 4 h. It was subsequently poured onto 600 g of ice, and 500 ml of EA were added; this mixture was washed 3× with 100 ml of a saturated aqueous solution of Na$_2$SO$_3$ on each occasion. The organic phase is now concentrated in vacuo and the residue was taken up once again with 500 ml of EA; this solution is washed 3× with 200 ml of a 0.6 M aqueous solution of KH$_2$PO$_4$ on each occasion. The organic phase was then stirred for 1 h together with 100 ml of a 2 N aqueous solution of HCl and the EA phase was then separated off. The aqueous phase was adjusted to pH 9 with Na$_2$CO$_3$ and extracted 3× with 200 ml of EA on each occasion. The organic phases were dried over Na$_2$SO$_4$ and the solvent was removed in vacuo. 6.4 g of a colorless oil were obtained.

| R$_f$ (DIP) = 0.46 | MS (DCI): 287 (M + H)$^+$ |
|---|---| b) 4-Hydroxybenzenesulfonic acid N,N'-bis-t-butylimidoamide 2.9 g of 4-fluorobenzenesulfonic acid N,N'-bis-t-butylimidoamide and 3.4 g of CsOH (monohydrate) were stirred at 160–170° C. for 8 h in 25 ml of TMU. The mixture was then allowed to cool to RT, 100 ml of water and 50 ml of a saturated aqueous solution of NaHCO$_3$ were added and the whole was extracted 3× with 100 ml of EA on each occasion. The organic phases were dried over Na$_2$SO$_4$ and the solvent was removed in vacuo. Chromatography on silica gel using EA/HEP 1:1 yields 700 mg of a colorless oil.

| R$_f$ (MTB/DIP 1.1) = 0.27 | MS (EI): 285 (M + H)$^+$ |
|---|---| c) Methyl 4-[4-(N-t-Butylimido-N'-t-butyl)sulf-amoyl]-phenoxy-3-trifluoromethylbenzoate 600 mg of 4-hydroxybenzenesulfonic acid N,N'-bis-t-butylimidoamide, 468 mg of methyl 4-fluoro-3-trifluoromethylbenzoate and 2.1 g of Cs$_2$CO$_3$ were stirred at 160° C. for 1.5 h in 10 ml of TMU. The mixture was allowed to cool to RT, 100 ml of a saturated aqueous solution of NaHCO$_3$ were added and the whole was extracted 3× with 100 ml of EA on each occasion. The organic phases were dried over Na$_2$SO$_4$ and the solvent was removed in vacuo. Chromatography on silica gel using DIP yields 400 mg of a colorless oil.

| R$_f$ (DIP) = 0.28 | MS (ES): 487 (M + H)$^+$ |
|---|---| d) 4-[4-(N-t-Butylimido-N'-t-butyl)sulfamoyl]phenoxy-3-trifluoromethylbenzoylguanidine 300 mg of methyl 4-[4-(N-t-butylimido-N'-t-butyl)sulfamoyl]-3-trifluoromethylbenzoate and 182 mg of guanidine were reacted in 10 ml of isopropanol in accordance with the general protocol for preparing benzoylguanidines, Variant B. 120 mg of a colorless oil were obtained.

| R$_f$ (EA) = 0.24 | MS (FAB): 587 (M + H)$^+$ |
|---|---| mp (dihydrochloride)=165–168° C.

EXAMPLE 3
4-[4-N-(Dimethylaminoethyl)methylsulfamoyl]-phenoxy-3 trifluoromethylbenzoylguanidine dihydrochloride

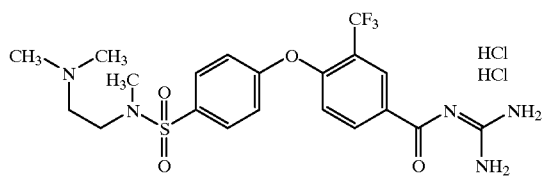

a) Methyl 4-phenoxy-3-trifluoromethylbenzoate 15 g of methyl 4-chloro-3-trifluoromethylbenzoate, 5.9 g of phenol and 17.4 g of K$_2$CO$_3$ were stirred at 110° C. for 14 h in 100 ml of DMF. The mixture was allowed to cool to RT, was diluted with 1 l of EA, and was then washed 2× with 200 ml of water on each occasion, 2× with 200 ml of a 0.1 N aqueous solution of NaOH on each occasion, and 2× with 300 ml of a saturated aqueous solution of NaCl on each occasion. The organic phase was dried over Na$_2$SO$_4$ and the solvent was removed in vacuo. Chromatography on silica gel using EA/HEP 1:8 yields 11 g of a colorless oil.

| $R_f$ (EA/HEP 1:8) = 0.24 | MS (DCI): 297 (M + H)$^+$ | b) 4-Phenoxy-3-trifluoromethylbenzoic acid 11 g of methyl 4-phenoxy-3-trifluoromethylbenzoate were dissolved in 200 ml of MeOH, 41 ml of a 1 N aqueous solution of NaOH were added and the mixture was stirred at RT for 24 h. The MeOH was then removed in vacuo, and the remaining mixture was diluted with 1 l of water and the whole adjusted to a pH of 2 with an aqueous solution of HCl; the precipitate was then filtered off. The latter was air-dried for 48 h, resulting in 9.2 g of an amorphous solid.

| $R_f$ (EA) = 0.10 | MS (DCI): 283 (M + H)$^+$ | c) 4-(4-Chlorosulfonyl)phenoxy-3-trifluoromethylbenzoic acid 1 g of 4-phenoxy-3-trifluoromethylbenzoic acid was dissolved in 15 ml of CHCl$_3$, and 710 µl of chlorosulfonic acid were added dropwise. The mixture was stirred at RT for 3 h and the solvent was then removed in vacuo. 50 g of ice and 50 ml of water were then added, and the mixture was stirred for 10 minutes and the precipitate then filtered off. 0.96 g of an amorphous solid were obtained.

| $R_f$ (DIP 2% HOAc) = 0.38 | MS (EI): 381 (M + H)$^+$ | d) 4-[4-N-(Dimethylaminoethyl)methylsulfamoyl]phenoxy-3-trifluoromethylbenzoic acid 475 mg of 4-(4-chlorosulfonyl)phenoxy-3-trifluoromethylbenzoic acid were dissolved in 10 ml of acetone, and 160 µl of trimethylethylenediamine and 350 µl of triethylamine were added. The mixture was stirred at RT for 2 h, after which it was diluted with 100 ml of water and the acetone was removed in vacuo. The remaining mixture was adjusted to pH=6–7 with a 0.1 N aqueous solution of HCl and then extracted 6× with 100 ml of EA on each occasion. The organic phases were dried over Na$_2$SO$_4$ and the solvent was removed in vacuo. 330 mg of an amorphous solid were obtained.

| $R_f$ (CH$_2$Cl$_2$/MeOH/HOAc/H$_2$O 8:4:1:1) = 0.42 | MS (EI): 447 (M + H)$^+$ | e) Methyl 4-[4-N-(Dimethylaminoethyl)methylsulfamoyl]-phenoxy-3-trifluoromethylbenzoate 330 mg of 4-[4-N-(dimethylaminoethyl)methylsulfamoyl]-phenoxy-3-trifluoromethylbenzoic acid and 1 ml of SOCl$_2$ were heated under reflux for 8 h in 10 ml of MeOH. The volatile constituents of the mixture were removed in vacuo, the residue was taken up with 100 ml each of a saturated aqueous Na$_2$CO$_3$ solution and 100 ml of EA and extracted 3× with 100 ml of EA on each occasion. The organic phases were dried over Na$_2$SO$_4$ and the solvent was removed in vacuo. Chromatography of the residue on silica gel using EA/MeOH 2:1 yields 150 mg of a colorless resin.

| $R_f$ (EA/MeOH 1:1) = 0.30 | MS (EI): 461 (M + H)$^+$ | f) 4-[4-N-(Dimethylaminoethyl)methylsulfamoyl]phenoxy-3-trifluoromethylbenzoylguanidine 140 mg of methyl 4-[4-N-(dimethylaminoethyl)methyl-sulfamoyl]phenoxy-3-trifluoromethylbenzoate and 90 mg of guanidine were reacted in 3 ml of isopropanol in accordance with the general protocol for preparing benzoylguanidines, Variant B. 130 mg of an amorphous solid were obtained.

| $R_f$ (EA/MeOH 1:1) = 0.12 | MS (EI): 488 (M + H)$^+$ |
| mp (dihydrochloride) = 203° C. | |

The title compounds of Examples 4–8 were synthesized in analogy with Example 3:

EXAMPLE 4

4-[4-(4-Methylpiperazinosulfonyl)phenoxy]-3-trifluoromethylbenzoylguanidine dihydrochloride

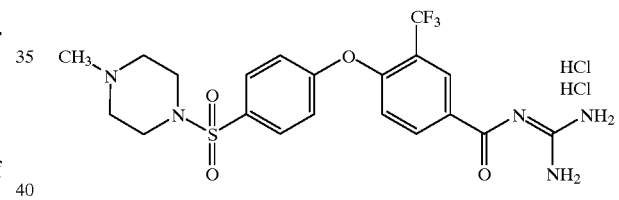

| $R_f$ (EA/MeOH 1:1) = 0.15 | MS(EI): 486(M + H)$^+$ |
| mp (dihydrochloride) > 250° C. | |

EXAMPLE 5

4-[4-(2-Pyrrolidineethylaminosulfonyl)-phenoxy]-3-trifluoromethylbenzoylguanidine dimaleate

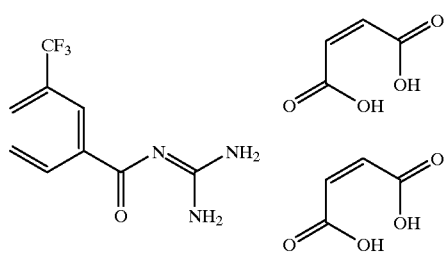

| $R_f$ (CH$_2$Cl$_2$/MeOH/HOAc/H$_2$O 8:4:1:1) = 0.37 | MS(FAB): 500(M + H)$^+$ |

EXAMPLE 6

4-[4-(2-Piperidineethylaminosulfonyl)phenoxy]-3-trifluoromethylbenzoylguanidine dimaleate

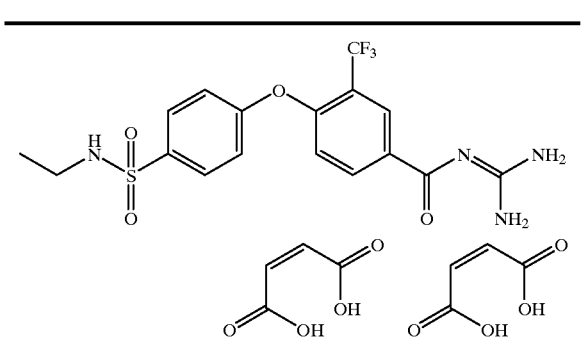

$R_f(CH_2Cl_2/MeOH/HOAc/H_2O\ 8:4:1:1) = 0.40$   MS(FAB): 514(M + H)$^+$

EXAMPLE 7

4-[4-(N-Dimethylamino-n-propyl)sulf-amoyl]-phenoxy-3-trifluoromethylbenzoylguanidine

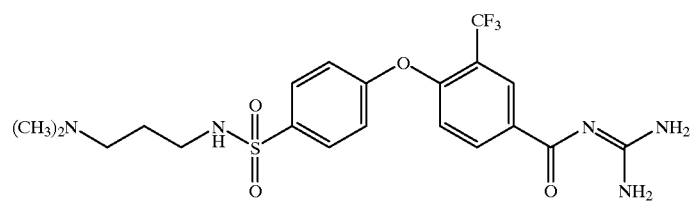

$R_f$ (EA/MeOH 1:1) = 0.06   MS(EI): 488(M + H)$^+$

EXAMPLE 8

4-[4-(N-Dimethylaminoethyl)sulfamoyl]phenoxy-3-trifluoromethylbenzoylguanidine

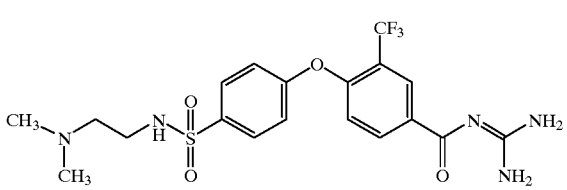

$R_f$ (EA/MeOH 1:1) = 0.17   MS(EI): 474(M + H)$^+$

EXAMPLE 9

4-(4-Imidosulfamoyl)phenoxy-3-trifluoromethylbenzoylguanidine

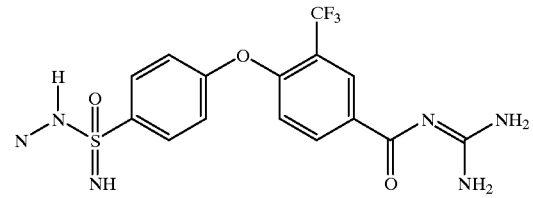

a) 4-[4-(t-Butylimido-N'-t-butyl)sulfamoyl]phenoxy-3-trifluoromethylbenzoic acid 7.9 g of methyl 4-[4-(N-t-butylimido-N'-t-butyl)sulfamoyl]phenoxy-3trifluoromethylbenzoate (Example 2c) were dissolved in 100 ml of MeOH, and 40 ml of a 2 N aqueous solution of NaOH were added. The mixture was boiled under reflux for 3 h, the MeOH was removed in vacuo and the residue was taken up in a mixture composed of 100 ml of water and 100 ml of EA. 500 ml of a saturated aqueous solution of NaH$_2$PO$_4$ were added and the whole was extracted 3 times with 200 ml of EA on each occasion. The organic phases were dried over Na$_2$SO$_4$ and the solvent was removed in vacuo. 7.2 g of white crystals were obtained.

$R_f$ (MTB) = 0.25   MS (ES): 473 (M + H)$^+$
mp = 200° C.

b) 4-(4-Imidosulfamoyl) phenoxy-3-trifluoromethylbenzoic acid 6.6 g of 4-[4-(N-t-butylimido-N'-t-butyl)sulfamoyl) phenoxy-3-trifluoromethylbenzoic acid were dissolved in 140 ml of anhydrous CH$_2$Cl$_2$, 3.7 ml of trifluoromethanesulfonic acid were added and the mixture was stirred at RT for 24 h. It was then stirred into 1 l of a 0.66 M aqueous solution of KH$_2$PO$_4$, and the methylene chloride phase was separated off and extracted 3 times with 300 ml of EA on each occasion. The combined organic phases were dried over Na$_2$SO$_4$ and the solvents were removed in vacuo. 6.7 g were obtained of a viscous oil which was used without further purification.

$R_f$ (EA/MeOH 5:1) = 0.21   MS (ES): 361 (M + H)$^+$ c) Methyl 4-(4-imidosulfamoyl)phenoxy-3-trifluoromethylbenzoate and
d) Methyl 4-(4-N-methylimidosulfamoyl)phenoxy-3-trifluoromethylbenzoate 6.7 g of 4-(4-imidosulfamoyl)phenoxy-3-trifluoromethylbenzoic acid were dissolved in 100 ml of MeOH, 20 ml of a 2 N solution of (trimethylsilyl) diazomethane in HEP were added dropwise, and the mixture was stirred at RT for 6 h. 200 ml of a 20% aqueous solution of acetic acid were then added and the whole was stirred for 30 minutes. 200 ml of EA were then added and this mixture was then extracted 9 times with 100 ml of a 1 N aqueous solution of HCl on each occasion. The aqueous phase was then adjusted to a pH of 10 with $Na_2CO_3$ and extracted 3 times with 200 ml of EA on each occasion. The organic phases were dried over $Na_2SO_4$ and the solvent was removed in vacuo. The residue was chromatographed on silica gel using EA/HEP 1:1 and 1.2 g of Product c) were obtained in addition to 890 mg of Product d), with both products being oils.

| | |
|---|---|
| c) $R_f$ (EA) = 0.32 | MS (ES): 375 (M + H)$^+$ |
| d) $R_f$ (EA) = 0.38 | MS (ES): 389 (M + H)$^+$ | e) 4-(4-Imidosulfamoyl)phenoxy-3-trifluoromethylbenzoylguanidine 220 mg of methyl 4-(4-imidosulfamoyl)phenoxy-3-trifluoromethylbenzoate and 174 mg of guanidine were reacted in 10 ml of THF in accordance with Variant B of the general protocol for preparing benzoylguanidines. 80 mg of colorless crystals were obtained following chromatography on silica gel using EA/MeOH 5:1.

| | |
|---|---|
| $R_f$ (EA/MeOH 5:1) = 0.22 | MS (ES): 402 (M + H)$^+$ |
| Mp = 156° C. | |

EXAMPLE 10
3-Trifluoromethyl-4-(4-N-methylimido-sulfamoyl) phenoxybenzoylguanidine

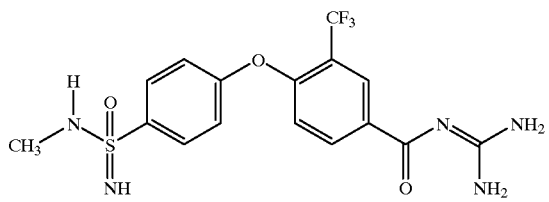

490 mg of methyl 4-(4-N-methylimidosulfamoyl) phenoxy-3-trifluoromethylbenzoate (Example 9d) and 373 mg of guanidine were reacted in 20 ml of THF in accordance with Variant B of the general protocol for preparing benzoylguanidines. 370 mg of colorless crystals were obtained following chromatography on silica gel using

| | |
|---|---|
| $R_f$ (EA/MeOH 5:1) = 0.33 | MS (ES): 416 (M + H)$^+$ |
| mp (dihydrochloride) = 233° C. | |

The title compound of Example 11 was synthesized from methyl 3-methyl-4-phenoxybenzoate in analogy with Example 3:

EXAMPLE 11
3-Methyl-4-(4-(1-methylpiperazin-4-yl-sulfonyl)phenoxy) benzoylguanidine

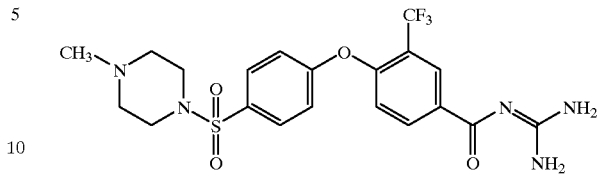

a) Methyl 3-methyl-4-phenoxybenzoate 3.4 g of methyl 4-fluoro-3-methylbenzoate, 2.4 g of phenol and 19.5 g of $Cs_2CO_3$ were stirred at 160° C. for 20 minutes in 100 ml of NMP. The mixture was poured into 400 ml of a saturated aqueous solution of $NaHCO_3$ and the whole was diluted with 400 ml of water and extracted 3 times with 200 ml of MTB on each occasion. The organic phases were dried over $Na_2SO_4$ and the solvent was removed in vacuo. Chromatographing the residue on silica gel using EA/HEP 1:4 yields 2.0 g of a colorless oil.

| | |
|---|---|
| $R_f$ (EA/HEP 1:4) = 0.33 | MS (EI): 243 (M + H)$^+$ |

The title compound of Example 12 was synthesized in analogy with Example 9:

EXAMPLE 12
3-Methylsulfonyl-4-(4-imidosulfamoyl) phenoxybenzoylguanidine

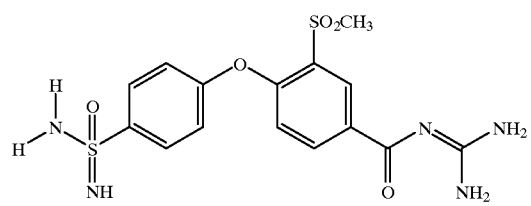

| | |
|---|---|
| $R_f$ (EA/MeOH 5:1) = 0.24 | MS(ES): 412(M + H)$^+$ |

EXAMPLE 13
4-(4-Guanidinosulfonyl)phenoxy-3-trifluoromethylbenzoylguanidine

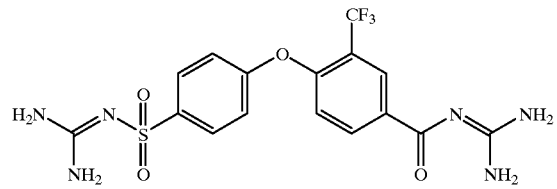

a) 4-(4-Hydroxysulfonyl) phenoxy-3-trifluoromethylbenzoic acid 13.5 g of 4-phenoxy-3-trifluoromethylbenzoic acid (Example 3b) were dissolved in 150 ml of $CHCl_3$, 3.3 ml of chlorosulfonic acid were added dropwise at RT and the mixture was subsequently stirred for 3 h. The solvent was removed in vacuo, 300 g of ice and 100 ml of water were added, and the mixture was stirred for 10 minutes. 400 ml of a saturated aqueous solution of NaCl which has been cooled to 0° C. were then added and the mixture was stirred at 0° C. for a further 15 minutes and the precipitate was filtered off with suction. It was dried in vacuo at 40° C. resulting in 16.5 g of a white solid which was subjected to further use without purification.

b) 4-(4-Chlorosulfonyl) phenoxy-3-trifluoromethylbenzoyl chloride 14.0 g of 4-(4-hydroxysulfonyl)phenoxy-3-trifluoromethylbenzoic acid and 1 ml of DMF were dissolved in 250 ml of $SOCl_2$ and this solution was heated under reflux for 8 h. Approximately half of the excess $SOCl_2$ was then removed in vacuo and the solution was added dropwise to 1 kg of ice. The mixture was extracted 3 times with 500 ml of $CH_2Cl_2$ on each occasion and the organic phases were dried over $MgSO_4$ and the solvent was removed in vacuo. 18.0 g were obtained of an oil which was used without further purification.

$R_f$(DIP/2% HOAc)=0.51 c) 3-Hydroxypyridyl 4-[4-(3-pyridyloxy)sulfonyl]phenoxy-3-trifluoromethylbenzoate 18.0 g of 4-(4-chlorosulfonyl)phenoxy-3-trifluoromethylbenzoyl chloride were dissolved in 150 ml of acetone, 3.7 g of 3-hydroxypyridine and 11.0 g of $K_2CO_3$ were added and the reaction mixture was stirred at RT for 3 h. It was then poured into 500 ml of water and the whole was extracted 3 times with 300 ml of EA on each occasion. The organic phases were dried over $Na_2SO_4$, the solvent was removed in vacuo and the residue was chromatographed on silica gel using MTB/2% HOAc. 8.0 g of a yellowish oil are obtained.

$R_f$ (MTB/2% HOAc) = 0.29    MS (FAB): 517 (M + H)⁺ d) 4-(4-Guanidinosulfonyl)phenoxy-3-trifluoromethylbenzoylguanidine 3.0 g of 3-hydroxypyridyl 4-[4-(3-pyridyloxy)sulfonyl]-phenoxy-3-trifluoromethylbenzoate and 3.4 g of guanidine were dissolved in 10 ml of i-propanol and this solution was heated under reflux for 3 h. The solvent was removed in vacuo and the residue was taken up in 400 ml of water; the solution was adjusted to pH 8 with an aqueous solution of HCl and stirred at RT for 2 h. The precipitate was filtered off and chromatographed on silica gel using EA/MeOH 5:1. 272 mg of an amorphous solid were obtained.

$R_f$ (EA/MeOH 5:1) = 0.33    MS (ES): 445 (M + H)⁺

EXAMPLE 14
3-Methylsulfonyl-4-[4-(2-dimethylaminoethyl)-phenoxy]benzoylguanidine bis-methanesulfonate

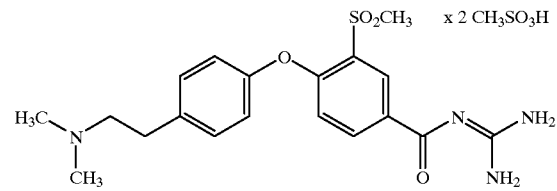

14 a) 5-Carboxy-2-fluorobenzenesulfinic acid 15.6 g (0.124 mol) of sodium sulfite were dissolved at 70° C. in 120 ml of water. While maintaining the same temperature, 23.8 g (0.1 mol) of 4-fluoro-3-chloro-sulfonylbenzoic acid and 10 N NaOH were added simultaneously and in portions in such a manner that the pH was maintained between 9 and 10 (exothermic reaction). The mixture was stirred at 70° C. for a further 3 hours, was subsequently left to stir for a further 15 minutes together with activated charcoal and was then filtered. The filtrate was adjusted to pH 0–1 with concentrated hydrochloric acid while cooling externally and the crystalline 5-carboxy-2-fluorobenzenesulfinic acid was filtered off.

Colorless crystals,
m.p.: 167–170° C.

14 b) 5-Carboxy-2-fluorobenzenesulfinic acid disodium salt was obtained by introducing 17.2 g (0.084 mol) of carboxy-2-fluorobenzenesulfinic acid into a stirred solution of 6.72 g (0.168 mol) of NaOH in a mixture composed of 150 ml of methanol and 30 ml of water: after removing suspended material by filtration, the solvent was distilled off and the residue was crystallized with acetone.

Colorless crystalline substance, m.p.: >320° C.

14 c) Methyl 4-fluoro-3-methylsulfonylbenzoate 30 g (0.21 mol) of methyl iodide were added to a suspension of 15 g (0.06 mol) of 5-carboxy-2-fluorobenzenesulfinic acid disodium salt in 80 ml of dry DMF and the mixture was stirred at 60° C. for 6 hours; the solvent was distilled off and water was added to the residue. This mixture was stirred for 30 min. while cooling with ice and the precipitate was filtered off.

Colorless crystalline substance,
m.p.: 102–105° C.

14 d) Methyl 3-methylsulfonyl-4-[4-(2-dimethylaminoethyl) phenoxy]benzoate 4.64 g (0.02 mol) of methyl 4-fluoro-3-methylsulfonylbenzoate were added to a mixture composed of 60 ml of dimethylacetamide, 3.6 g (0.022 mol) of N,N-dimethyl-2-(4-hydroxyphenyl)ethylamine and 9.08 g (0.066 mol) of powdered, anhydrous $K_2CO_3$, and the suspension was stirred at 90° C. for 4 hours. After distilling off the solvent and adding water to the residue, the latter mixture was extracted several times with ethyl acetate; the combined organic phases were then concentrated under reduced pressure and the substance was obtained as a yellow, oily liquid.

14 e) Preparation of 3-methylsulfonyl-4-[4-(2-dimethylaminoethyl)phenoxy]benzoic acid hydrochloride 1.88 g (0.005 mol) of methyl 3-methylsulfonyl-4-[4-(2 dimethylaminoethyl)phenoxy]benzoate were boiled under reflux for 5 hours in 40 ml of half-concentrated hydrochloric acid, after which the aqueous hydrochloric acid was distilled off and the residue was crystallized with acetone.

Colorless crystalline substance, m.p.: 246–248° C.

14 f) 3-Methylsulfonyl-4-[4-(2-dimethylaminoethyl) phenoxy]benzoylguanidine was obtained, in analogy with the protocol given in Variant A, from 3-methylsulfonyl-4-[4-(2-dimethylamino-ethyl)phenoxy]benzoic acid at a pH of between 7 and 8.

Colorless crystals, m.p.: 214–218° C.

3-Methylsulfonyl-4-[4-(2-dimethylaminoethyl)phenoxy] benzoylguanidine bis-methanesulfonate was obtained, in analogy with the protocol given in Variant A, from 3-methylsulfonyl-4-[4-(2-dimethylamino-ethyl)phenoxy] benzoylguanidine by treating it with 2.5 eq of methanesulfonic acid in ethanol.

Colorless solid, m.p.: 102° C.

EXAMPLE 15

4-[4-(2-Dimethylaminoethyl)thiomethyl-phenoxy]-3-methylsulfonylbenzoylguanidine dihydrochloride

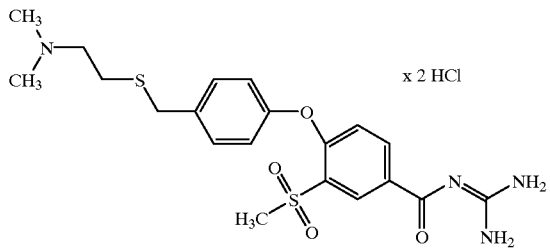

15 a) Preparation of 4-(2-dimethylaminoethyl)-thiomethylphenol

A mixture composed of 200 mg of p-toluenesulfonic acid, 14.1 g (0.1 mol) of 2-dimethylaminoethylmercaptan hydrochloride and 12.4 g (0.1 mol) of 4-hydroxybenzyl alcohol in 250 ml of toluene was boiled, under reflux for about 5 hours, on a Kutscher and Steudel water separator, the solvent was then driven off and the residue was dissolved in methanol after which this solution was filtered. After concentrating once again, the residue was crystallized from acetone, the crystalline product was filtered off and the slightly hygroscopic mass was dried over NaOH while excluding air.

m.p.: 134–140° C.

15 b) Methyl 4-[4-(2-dimethylaminoethyl) thiomethylphenoxy]-3 methylsulfonylbenzoate A mixture composed of 3.48 g (0.015 mol) of 4-(2-dimethylaminoethyl)thiomethylphenol, 40 ml of anhydrous tetramethylurea, 6.8 g (0.049 mol) of anhydrous powdered K$_2$CO$_3$ and 3.48 g (0.015 mol) of methyl 4-fluoro-3-methylsulfonylbenzoate was stirred at 90–100° C. for 6 hours, the solvent was distilled off and the residue was taken up in water. After extracting with ethyl acetate, and drying and concentrating the combined organic phases, the desired product was obtained as an oil.

15 c) 4-[4-(2-Dimethylaminoethyl)thiomethylphenoxy]-3-methylsulfonylbenzoic acid hydrochloride was obtained, in analogy with the protocol described in Example 14d), by hydrolyzing methyl 4-fluoro-3-methyl-sulfonylbenzoate in 20% HCl.

Colorless to pale-yellow crystalline substance, m.p.: 179–185° C.

15 d) 4-[4-(2-Dimethylaminoethyl)thiomethylphenoxy]-3-methylsulfonylbenzoylguanidine dihydrochloride was obtained, in analogy with the protocol described in Example 14 e), from 4-[4-(2-dimethylaminoethyl) thiomethylphenoxy]-3-methylsulfonylbenzoic acid hydrochloride.

Hygroscopic substance, m.p.: 230° C.

EXAMPLE 16

4-[4-(2-Dimethylaminoethylthio)phenoxy]-3-methylsulfonylbenzoylguanidine dihydrochloride

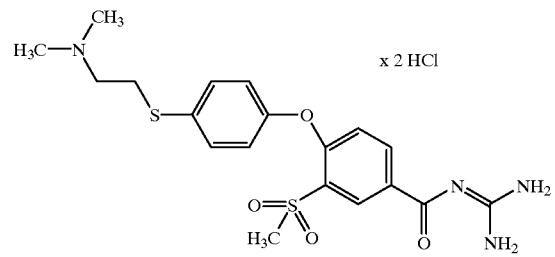

16 a) N,N-Dimethyl-2-(4-hydroxyphenylthio) ethylamine 17.28 g (0.11 mol) of 2-dimethylaminoethyl chloride hydrochloride, and then 19.38 g (0.15 mol) of ethyl diisopropylamine, were added, under an atmosphere of protective gas (argon), to a solution of 12.6 g (0.1 mol) of 4-mercaptophenol in 100 ml of anhydrous DMF, and the reaction mixture was heated at 110° C. for 12 hours while stirring with a magnet. After the solvent had been distilled off, water was added to the residue and this mixture was adjusted to pH 8–9 with 2 N NaOH; the amorphous precipitate was extracted several times with ethyl acetate and the combined organic phases were dried over sodium sulfate. The solvent was distilled off and the residue was subjected to column chromatography on silica gel, being eluted with a mixture composed of 8 parts of ethyl acetate and 1 part of methanol.

Colorless crystals, m.p. 108–110° C.

16 b) Methyl 4-[4-(2-dimethylaminoethylthio)phenoxy]-3-methylsulfonyl-benzoate was obtained as a yellow oil, in analogy with the protocol described in 14 d), by reacting N,N-dimethyl-2-(4-hydroxyphenylthio) ethylamine with methyl 4-fluoro-3 -methylsulfonylbenzoate, with DMF being used as the reaction medium in place of dimethylacetamide. Yellow oily liquid.

16 c) 4-[4-(2-Dimethylaminoethylthio)phenoxy]-3-methyl-sulfonylbenzoic acid 6.8 g of methyl 4-[4-(2-dimethylaminoethylthio) phenoxy]-3-methylsulfonylbenzoate are boiled, under reflux conditions for 5 hours, in 10 ml of glacial acetic acid and 70 ml of half-concentrated HCl. After the solvent had been distilled off, the desired substance was obtained as an amorphous solid which does not have a defined melting point.

16 d) 4-(4-(2-Dimethylaminoethylthio) phenoxy]-3-methyl-sulfonylbenzoylguanidine dihydrochloride was obtained in analogy with the protocol given in Variant A.

Colorless solid,

Decomposition point: 160° C. with foaming.

EXAMPLE 17
4-[4-(2-Dimethylaminoethylsulfonyl) phenoxy]-3-methylsulfonylbenzoylguanidine dihydrochloride

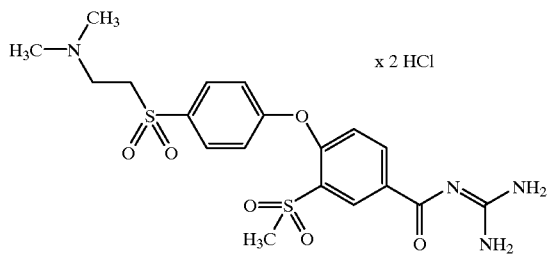

17 a) 4-[4-(2-Dimethylaminoethylsulfonyl) phenoxy]-3-methylsulfonylbenzoic acid 6.9 g (0.028 mol) of 3-chloroperbenzoic acid were added, in portions at 5–10° C., to a solution of 3.8 g (0.008 mol) of 4-[4-(2-dimethylaminoethylthio)phenoxy]-3-methylsulfonylbenzoic acid in 50 ml of glacial acetic acid and the mixture was stirred at RT for 12 hours. After having added water, the precipitate of 3-chlorobenzoic acid was filtered off and further impurities were extracted from the filtrate using ethyl acetate. The aqueous phase was concentrated and the amorphous residue was crystallized with ethyl acetate. Colorless crystals, m.p.: 167–171° C.

17 b) 4-[4-(2-Dimethylaminoethylsulfonyl)phenoxy]-3-methylsulfonylbenzoylguanidine dihydrochloride was obtained, in analogy with the protocol given in Variant A, from 4-[4-(2-dimethylaminoethylsulfonyl)-phenoxy]-3-methylsulfonylbenzoic acid in TMU as the reaction medium. The dihydrochloride was crystallized with methanol.

Colorless crystals,
m.p.: 233–240° C. (decomposition).

EXAMPLE 18
4-[(4-Guanidinocarbonyl)phenoxy]-3-methyl-sulfonylbenzoylguanidine dihydrochloride

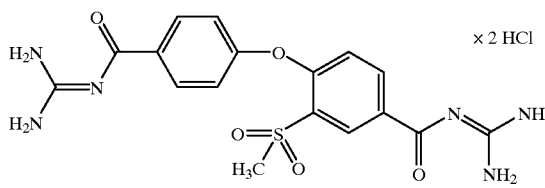

18 a) 4-(4-Carboxyphenoxy)-3-methylsulfonylbenzoic acid

By reacting ethyl 4-hydroxybenzoate with methyl 4-fluoro-3-methylsulfonylbenzoate in analogy with the protocol given under 14 d) methyl 4-(4-ethoxycarbonylphenoxy)-benzoate was obtained as a colorless to pale-yellow oil which was hydrolyzed, without any further purification steps, in analogy with the manner indicated in protocol 16 c), to give 4-(4-carboxyphenoxy)-3-methylsulfonyl-benzoic acid.

Colorless crystals,
m.p.: 272–275° C.

18 b) 4-[(4-Guanidinocarbonyl)phenoxy]-3-methylsulfonyl-benzoylguanidine dihydrochloride was obtained, in analogy with the protocol described in Variant A, by reacting 0.74 g (0.0022 mol) of (4-carboxy-phenoxy)-3-methylsulfonylbenzoic acid with 0.78 g (0.0048 mol) of carbonyldiimidazole and 1.55 g (0.026 mol) of guanidine in DMA.

Colorless crystals,
m.p.: 252° C. (decomposition).

EXAMPLE 19
4-[4-(2-Dimethylaminoethyl)thiomethyl-phenoxy]-3-trifluoromethylbenzoylguanidine dihydrochloride

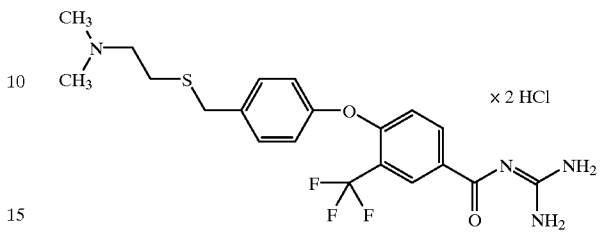

19 a) Methyl 4-[4-(2-dimethylaminoethyl) thiomethylphenoxy]-3-trifluoromethylbenzoate was obtained, in analogy with the protocol described in Example 15b), from 4-(2-dimethylaminoethyl)-thiomethylphenol and methyl 4-fluoro-3-trifluoromethyl-benzoate, in DMU as the reaction medium, as an amorphous, oily product.

19 b) 4-[4-(2-Dimethylaminoethyl) thiomethylphenoxy]-3-trifluoromethylbenzoic acid was obtained, in analogy with the protocol described in Example 14 d), by acid hydrolysis of methyl 4-[4-(2-dimethylaminoethyl) thiomethylphenoxy]-3-trifluoromethylbenzoate.

Colorless, hygroscopic crystals,
m.p.: 158–168° C. (decomposition).

19 c) 4-[4-(2-Dimethylaminoethyl) thiomethylphenoxy]-3-trifluoromethylbenzoylguanidine dihydrochloride was obtained, in analogy with the protocol described in Variant A, from 4-[4-(2-dimethylaminoethyl) thiomethylphenoxy]-3-trifluoromethylbenzoic acid in TMU as the reaction medium. Amorphous, strongly hygroscopic solid, decomposition at 80–85° C.

EXAMPLE 20
4-[4-(2-Dimethylaminoethylthio)phenoxy]-3-trifluoromethylbenzoylguanidine dihydrochloride

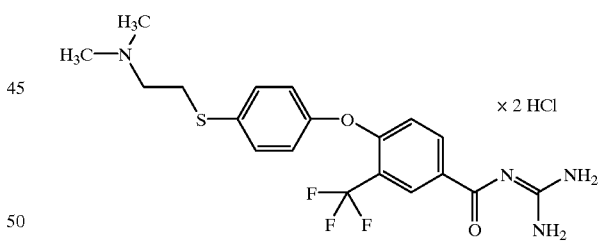

20 a) Methyl 4-[4-(2-dimethylaminoethylthio)phenoxy]-3-trifluoromethylbenzoate is obtained, in analogy with the protocol described in Example 15 b), from 4-(2-dimethylaminoethylthio)phenol and methyl 4-fluoro-3-trifluoromethylbenzoate, in DMU as the reaction medium, as an amorphous, oily product.

20 b) 4-[4-(2-Dimethylaminoethylthio)phenoxy]-3-trifluoromethylbenzoic acid is obtained, in analogy with the protocol described in Example 14d), by acid hydrolysis of methyl 4-[4-(2-dimethylaminoethylthio)phenoxy]-3-trifluoromethylbenzoate. The desired 4-[4-(2-dimethylaminoethylthio) phenoxy]-3-trifluoromethylbenzoic acid is crystallized with acetone.

Colorless crystals,
m.p. 174–182° C. (decomposition)

20 c) 4-[4-(2-Dimethylaminoethylthio)phenoxy]-3-trifluoromethylbenzoylguanidine dihydrochloride is obtained, in analogy with the protocol described in Variant A, from 4-[4-(2-dimethylaminoethylthio)phenoxy]-3-trifluoromethylbenzoic acid in THF as the reaction medium.

Amorphous, hygroscopic crystalline solid,
m.p.: 240° C.

EXAMPLE 21
3-Trifluoromethyl-4-[4-(2-dimethyl-aminoethyl) phenoxy] benzoylguanidine dihydrochloride

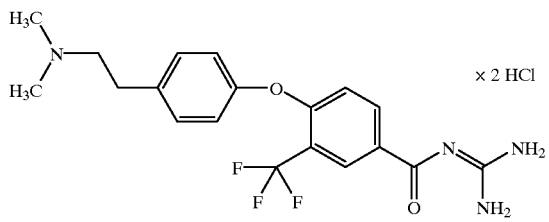

21 a) 4-Chloro-3-trifluoromethylbenzoic acid

The Grignard compound was initially prepared from 100 g of 5-bromo-2-chlorobenzotrifluoride and 10.2 g of magnesium in 600 ml of diethyl ether. A stream of 60 g of anhydrous $CO_2$ was then passed into this solution at RT. 500 ml of a saturated aqueous solution of $NaHSO_4$ were added dropwise and the phases were separated; further extraction took place with 2×100 ml of diethyl ether. The organic phase was extracted 3× with 300 ml of 1 N NaOH on each occasion, and the aqueous phase was then washed 3× with 100 ml of diethyl ether on each occasion. The aqueous phase was now brought to pH 2 with HCl and diluted to 4 l with water. The product was filtered off with suction and dried in vacuo.

75 g of white powder.

$R_f$(MTB 2% HOAc)=0.68

21 b) Methyl 4-chloro-3-trifluoromethylbenzoate 75 g of 4-chloro-3-trifluoromethylbenzoic acid were dissolved in 500 ml of MeOH, and 75 ml of $SOCl_2$ were added dropwise. The mixture was boiled under reflux for 5 h and the volatile constituents were then removed in vacuo. The residue was taken up in 1 l of EA and this solution was washed with 500 ml of a saturated aqueous solution of $Na_2CO_3$. The organic phase was then dried over $Na_2SO_4$, the solvent was removed in vacuo and the product was distilled in vacuo.

| b.p. 94° C. (2 torr) | MS (DCI): 239 (M + H)$^+$ |
|---|---|
| $R_f$ (DIP) = 0.49 | |

21 c) Methyl 4-[4-(2-dimethylaminoethyl)phenoxy]-3-trifluoromethylbenzoate 1.9 g of methyl 4-chloro-3-trifluoromethylbenzoate, 1.3 g of 4-(2-dimethylamino) ethylphenol and 7.8 g of $Cs_2CO_3$ were stirred, at 140° C. for 5 h, in 50 ml of tetramethylurea. The mixture was allowed to cool and 300 ml of a saturated aqueous solution of $NaHCO_3$ and 150 ml of water were then added and the whole was extracted 3× with 100 ml of EA on each occasion. The organic phases were dried over $Na_2SO_4$ and the solvent was then removed in vacuo. Chromatography using acetone/water 10:1 yields 2.0 g of a colorless oil.

Rf (acetone/water 10:1)=0.15

MS (DCI): 368 (M+H)$^+$ 21 d) 4-[4-(2-Dimethylaminoethyl)phenoxy]-3-trifluoromethylbenzoylguanidine 2.0 g of methyl 4-[4-(2-dimethylaminoethyl)phenoxy]-3-trifluoromethylbenzoate were guanylated with 1.6 g of guanidine in 60 ml of isopropanol in accordance with Variant B. The crude product was converted into the dihydrochloride and recrystallized from 1,2-dimethoxy-ethane/water 9:1.

m.p. (free base): 164° C.

m.p. (dihydrochloride): 236° C. MS (DCI): 395 (M+H)+
Solubility of the dihydrochloride in water, 49 mg/ml (pH=5.3)

EXAMPLE 22

4-[4-(2-N,N-Dimethylamino)ethyl]phenoxy)-3-sulfamoylbenzoylguanidine bis-methanesulfonate

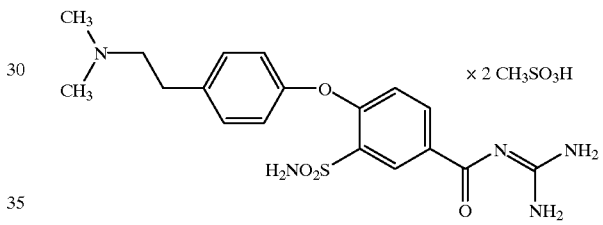

was obtained, in analogy with the protocol described in Variant A, from 4-[4-(2-dimethylaminoethyl)phenoxy]-3-sulfamoylbenzoic acid in dimethylacetamide or N-methylpyrrolidone as the reaction medium. Amorphous, hygroscopic, crystalline solid, m.p.: 183° C.

a) Methyl 4-[4-(2-dimethylaminoethyl)phenoxy]-3-sulfamoylbenzoate was obtained by heating 0.011 mol of N,N-dimethyl-2-(4-hydroxyphenyl) ethylamine, 0.033 mol of potassium carbonate (ground) and 0.01 mol of methyl 4-fluoro-3-sulfamoylbenzoate at 90–100° C. for 5 hours in 40 ml of dimethylacetamide. After the solvent had been distilled off, the residue was stirred with water and the brown amorphous product was treated with ethyl acetate; the crystalline precipitate was filtered off and the solvent was distilled off from the filtrate. Amorphous oily product.

b) 4-[4-(2-Dimethylaminoethyl)phenoxy]3-sulfamoylbenzoic acid was obtained by hydrolyzing 0.0066 mol of the corresponding methyl ester (a) for 5 hours in 60 ml of boiling half-concentrated hydrochloric acid. After the aqueous hydrochloric acid had been evaporated off in vacuo, the residue was treated with acetone and the precipitate was filtered off. The solvent was distilled off and the desired benzoic acid was obtained. Softening point from 60° C.

EXAMPLE 23

3-Chloro-4-[4-(2-dimethylaminoethyl)phenoxy]-5-methylsulfonylbenzoylguanidine bis-methanesulfonate

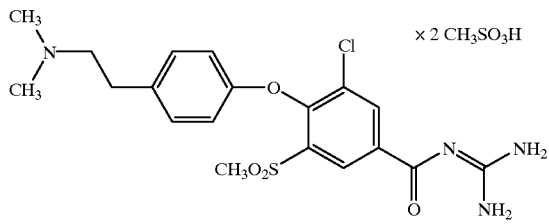

was obtained, in analogy with the protocol described in Variant A, from 3-chloro-4-[4-(2-dimethylaminoethyl)-phenoxy]-5-methylsulfonylbenzoic acid in dimethylacetamide or N-methylpyrrolidone as the reaction medium. Hygroscopic crystalline solid, m.p.: 200° C.

a) Methyl 3-chloro-4-[4-(2-dimethylaminoethyl) phenoxy]-5-methylsulfonylbenzoate was obtained, in analogy with Example 22 a), by reacting methyl 3,4-dichloro-5-methylsulfonylbenzoate with N,N-dimethyl-2-(4-hydroxyphenyl) ethylamine. Amorphous, oily substance.

b) 3-Chloro-4-[4-(2-dimethylaminoethyl)phenoxy]-5-methyl-sulfonylbenzoic acid was obtained in analogy with Example 22 a). Crystalline solid, Decomp. 238–244° C.

EXAMPLE 24

4-[(4-Guanidinocarbonyl)phenoxy]-3-methyl-sulfonylbenzoylguanidine

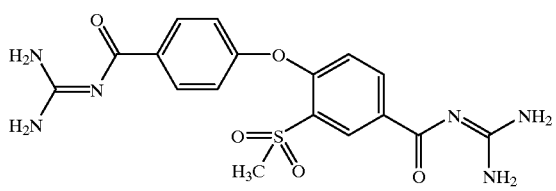

was obtained, as the salt-free base from Example 18, by treating 4-[(4-guanidinocarbonyl (phenoxy]-3-methyl-sulfonylbenzoylguanidine dihydrochloride with triethylamine in DNF.

Colorless crystalline solid, m.p.: 237° C.

EXAMPLE 25

4-[4-(2-N-Imidazolyl-1-oxoethyl)phenoxy]-3-methylsulfonylbenzoylguanidine dihydrochloride

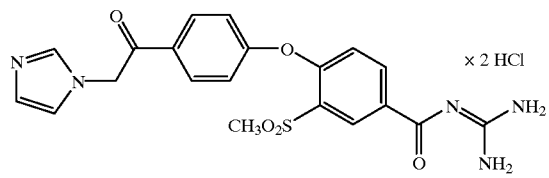

was obtained, in analogy with the protocol described in Variant A, from 4-[4-(2-N-imidazolyl-1-oxoethyl)phenoxy]-3-methylsulfonylbenzoic acid in dry dimethylacetamide or N-methylpyrrolidone as the reaction medium. Colorless crystalline solid, decomp.: 255° C.

a) 4-[4-Chloroacetylphenoxy)-3-methylsulfonylbenzoic acid 0.02 mol of 3-methylsulfonyl-4-phenoxybenzoic acid was introduced, in portions and at 0–5° C., into a mixture composed of 0.08 mol of chloroacetyl chloride, 16 g of anhydrous aluminum chloride and 150 ml of 1,2-dichloroethane and the mixture was stirred at room temperature for 2 hours and then at 40–45° C. for 2 hours. After having been left to stand overnight, the reaction mixture was poured, while stirring, into ice water and the crystalline precipitate was filtered off, washed with water and dried. Yellow crystals, m.p.: 184–187° C.

b) 4-[4-(2-N-Imidazolyl-1-oxoethyl)phenoxy]-3-methyl-sulfonylbenzoic acid

A solution of 0.005 mol of 4-(4-chloroacetylphenoxy)-3-methylsulfonylbenzoic acid (25 a) in 25 ml of anhydrous DMF was stirred with 0.0225 mol of imidazole at 60° C. for 4 hours and the solvent was then distilled off. After the amorphous residue had been treated with water, and the pH had been adjusted to pH 2–3 with 2 N hydrochloric acid, the mixture was stirred for one hour and the crystalline precipitate was filtered off. Crystals, decomp. 235–241° C.

EXAMPLE 26

4-[4-(2-Imidazolylthioacetyl)phenoxy]-3-methylsulfonylbenzoylguanidine dihydrochloride

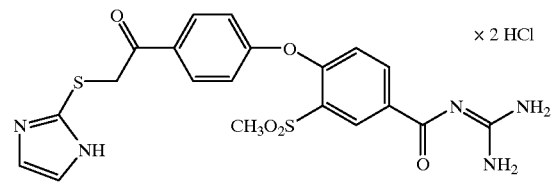

was obtained, in analogy with the protocol described in Variant A, from 4-[4-(2-imidazolylthioacetyl)phenoxy]-3-methylsulfonylbenzoic acid in a mixture composed of 50 ml of THF and 10 ml of dimethylacetamide as the reaction medium. Colorless crystalline solid, m.p.: 220° C.

a) 4-(4-(2-Imidazolylthioacetyl)phenoxy]-3-methyl-sulfonylbenzoic acid was obtained by reacting 4-(4-chloroacetylphenoxy)-3-methylsulfonylbenzoic acid (Example 25 a) and 1 mol of 2-mercaptoimidazole in 20 ml of acetone and briefly heating to boiling point. The mixture was stirred at room temperature for approximately 5 days and the crystalline precipitate was filtered off.

Decomp.: 202–205° C.

EXAMPLE 27

4-[4-(4,5-Dihydro-2-imidazolylthioacetyl)-phenoxy]-3-methylsulfonylbenzoylguanidine dihydrochloride

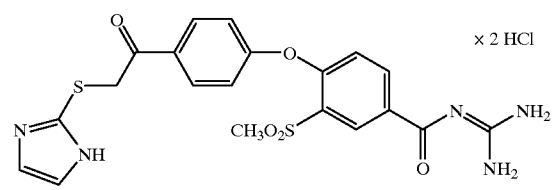

was obtained, in analogy with the protocol described in Variant A, from 4-[4-(4,5-dihydro-2-imidazolylthioacetyl) phenoxy]-3-methylsulfonylbenzoic acid in a mixture composed of 50 ml of THF and 10 ml of dimethylacetamide as the reaction medium.

Colorless crystalline solid, m.p.: 210° C.

a) 4-[4-(4,5-Dihydro-2-imidazolylthioacetyl)phenoxy]-3-methylsuylfonylbenzoic acid was prepared, in analogy with Protocol 26 a), by reacting 4-(4-chloroacetylphenoxy)-3-methylsulfonylbenzoic acid (Example 25a) with 2-mercapto-4,5-dihydroimidazole. Decomp.: 305–310° C.

EXAMPLE 28

4-[4-(N,N'-Dimethyl-S-isothiouronylacetyl)-phenoxy]-3-methylsulfonylbenzoylguanidine dihydrochloride

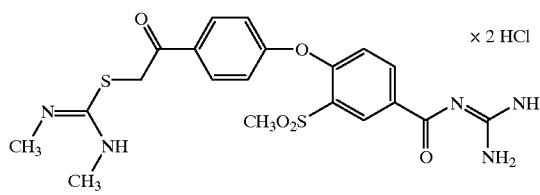

was obtained, in analogy with the protocol described in Variant A, from 4-[4-(N,N'-dimethyl-S-isothiouronylacetyl)phenoxy]-3-methylsulfonylbenzoic acid in a mixture composed of 50 ml of THF and 10 ml of dimethylacetamide as the reaction medium.

Colorless crystalline solid,
m.p.: 150° C.

a) 4-[4-(N,N'-Dimethyl-S-isothiouronylacetyl)phenoxy]-3-methylsulfonylbenzoic acid was obtained, in analogy with protocol 26 a), by reacting 4-(4-chloroacetylphenoxy)-3-methylsulfonylbenzoic acid (Example 25 a) with N,N'-dimethylthiourea at room temperature. Colorless crystals.
Decomp.: 185–190° C.

EXAMPLE 29

4-[4(2-Benzimidazolylthioacetyl)phenoxy]-3-methylsulfonylbenzoyguanidine dihydrochloride

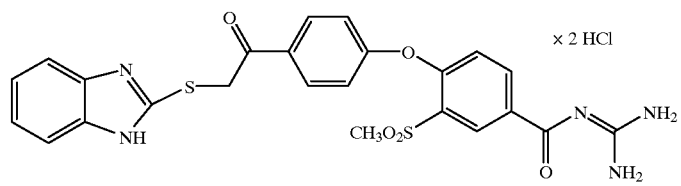

was obtained, in analogy with the protoccol described in Variant A, from 4-[4-(2-benzimidazolylthioacetyl)-phenoxy]-3-methylsulfonylbenzoic acid in THF as the reaction medium. Colorless crystalline solid, m.p. 228° C.

a) 4-[4-(2-Benzimidazolylthioacetyl)phenoxy]-3-methyl-sulfonylbenzoic acid was obtained, in accordance with protocol 26 a), by reacting 4-(4-chloroacetylphenoxy)-3-methylsulfonylbenzoic acid (Example 25 a) with 2-mercaptobenzimidazole in DMF.

m.p.: 182° C.

EXAMPLE 30

4-[4-(2-Pyridylthioacetyl)phenoxy]-3-methyl-sulfonylbenzoylguanidine dihydrochloride

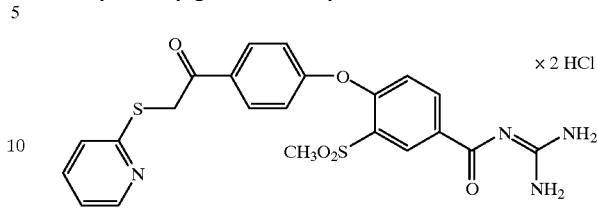

was obtained, in analogy with the protocol described in Variant A, from 4-[4-(2-pyridylthioacetyl)phenoxy]-3-methylsulfonylbenzoic acid in THF as the reaction medium. Colorless crystalline solid, m.p.: 203° C.

a) 4-[4-(2-Pyridylthioacetyl)phenoxy]-3-methylsulfonyl-benzoic acid was obtained, in analogy with protocol 26 a), by reacting 4-(4-chloroacetylphenoxy)-3-methylsulfonylbenzoic acid (Example 25 a) with 2-mercaptopyridine.

m.p.: 194–196° C.

EXAMPLE 31

4-[4-(2-Quinolylthioacetyl)phenoxy]-3-methyl-sulfonylbenzoylguanidine dihydrochloride

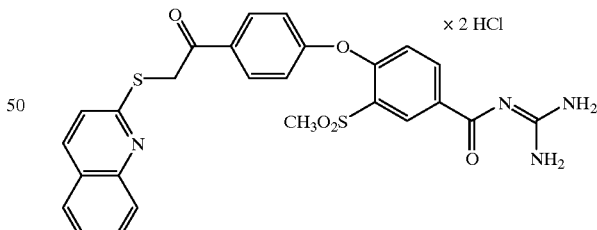

was obtained, in analogy with the protocol described in Variant A, from 4-[4-(2-quinolylthioacetyl)phenoxy]-3-methylsulfonylbenzoic acid in THF as the reaction medium. Colorless crystalline solid, m.p.: 192° C.

a) 4-[4-(2-Quinolylthioacetyl)phenoxy]-3-methylsulfonyl-benzoic acid was prepared, in analogy with Protocol 26 a), by reacting 4-(4-chloroacetylphenoxy)-3-methylsulfonylbenzoic acid (Example 25 a) with 2-mercaptoquinoline in DMF. m.p. 210–214° C.

EXAMPLE 32
4-[4-(2-N-imidazolyl-1-hydroxyethyl)phenoxy]-3-methylsulfonylbenzoylguanidine dihydrochloride

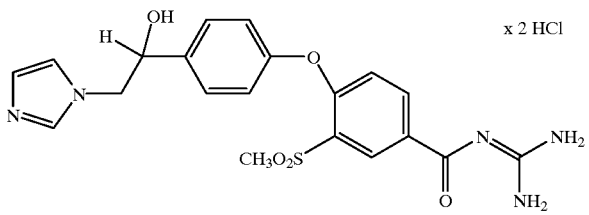

was obtained, in analogy with the protocol described in Variant A, from 4-[4-(2-N-imidazolyl-1-hydroxyethyl)-phenoxy]-3-methylsulfonylbenzoic acid in dimethylacetamide or N-methylpyrrolidine as the reaction medium. Colorless crystalline solid, decomposition point: 260° C.

a) 4-[4-(2-N-imidazolyl-1-hydroxyethyl) phenoxy]-3-methyl-sulfonylbenzoic acid was obtained by reducing 0.0034 mol of 4-[4-(2-N-imidazolyl-1-oxoethyl)phenoxy]-3-methyl-sulfonylbenzoic acid with 0.0068 mol of sodium borohydride in 40 ml of ethanol. After distilling off the solvent, treating the residue with water and adjusting the pH to 4 with 2 N HCl, the mixture was stirred for a few hours at room temperature and the crystals were filtered off.

m.p. 240–248° C.

EXAMPLE 33
3-Methylsulfonyl-4-(4-sulfamoylphenoxy)-benzoylguanidine hydrochloride

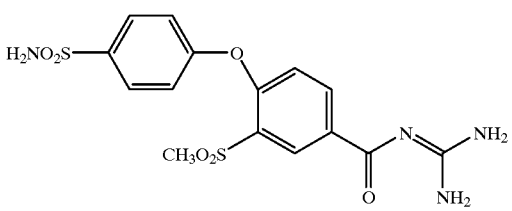

was obtained, in analogy with the protocol described in Variant A, from 3-methylsulfonyl-4-(4-sulfamoyl-phenoxy) benzoic acid in dimethylacetamide as the reaction medium. Colorless crystalline solid, decomposition point: 267° C.

a) 3-Methylsulfonyl-4-(4-chlorosulfonylphenoxy) benzoic acid was obtained by reacting 0.03 mol of 4-phenoxy-3-methyl-sulfonylbenzoic acid with 0.15 mol of chlorosulfonic acid in 60 ml of methylene chloride at 0–5° C. and subsequently stirring the mixture at room temperature for 4 hours. After the mixture had been treated with ice water, the methylene chloride phase was separated off, washed with water and dried over magnesium sulfate, and the solvent was then distilled off. Crystals, m.p.: 167–170° C.

b) 3-Methylsulfonyl-4-(4-sulfamoylphenoxy)benzoic acid was obtained by reacting 3-methylsulfonyl-4-(4-chlorosulfonylphenoxy)benzoic acid with an aqueous concentrated solution of ammonia at room temperature for 24 hours, distilling off the ammonia and acidifying the aqueous solution to pH 1–2 with 2 N HCl. The crystals were filtered off, washed with water and dried. Colorless crystalline substance, m.p. 240–245° C.

EXAMPLE 34
4-[4-(1-Hydroxy-2-(2-pyridylthio)ethyl)-phenoxy]-3-methylsulfonylbenzoylguanidine dihydrochloride

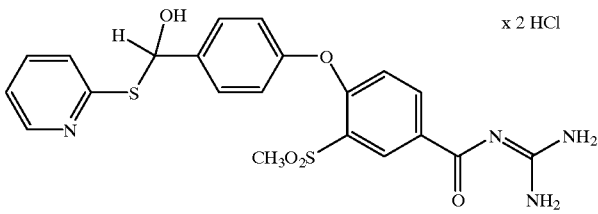

was obtained, in analogy with the protocol described in Variant A, from 4-[4-(1-hydroxy-2-(2-pyridylthio)ethyl)-phenoxy]-3-methylsulfonylbenzoic acid in THF as the reaction medium. Colorless crystalline solid, m.p.: 116° C.

a) 4-[4-(1-Hydroxy-2-(2-pyridylthio)ethyl)phenoxy]-3-methylsulfonylbenzoic acid was obtained in analogy with Example 32 a). Colorless crystalline substance, m.p.: 169–174° C.

EXAMPLE 35
4-[4-(1-Hydroxy-2-(2-benzimidazolylthio)-ethyl)phenoxy]-3-methylsulfonylbenzoylguanidine dihydrochloride

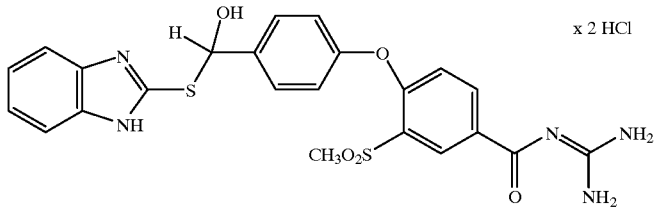

was obtained, in analogy with the protocol described in Variant A, from 4-[4-(1-hydroxy-2-(2-benzimidazolylthio)-ethyl)phenoxy]-3-methylsulfonylbenzoic acid in dimethylacetamide as the reaction medium. Colorless crystalline solid,
m.p.: 213° C.

a) 4-[4-(1-Hydroxy-2-(2-benzimidazolylthio)ethyl)-phenoxy]-3-methylsulfonylbenzoic acid was obtained in analogy with Example 32 a). Colorless crystalline substance,
m.p.: 186–188° C.

EXAMPLE 36
4-[4-(1-Hydroxy-2-(2-quinolylthio)ethyl)-phenoxy]-3-methylsulfonylbenzoylguanidine dihydrochloride

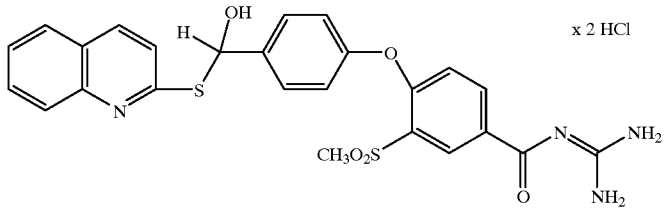

was obtained, in analogy with the protocol described in Variant A, from 4-[4-(1-hydroxy-2-(2-quinolylthio)ethyl)-phenoxy]-3-methylsulfonylbenzoic acid in THF as the reaction medium. Colorless crystalline solid, m.p.: 180° C.

a) 4-[4-(1-Hydroxy-2-(2-quinolylthio)ethyl)phenoxy]-3-methylsulfonylbenzoic acid was obtained, in analogy with Example 32 a), from 4-[4-(2-quinolylthioacetyl) phenoxy]-3-methylsulfonylbenzoic acid (Example 31 a). Colorless crystalline substance.

EXAMPLE 37
4-[4-(N,N-Dimethylglycylamino)phenoxy]-3-methylsulfonylbenzoylguanidine dihydrochloride

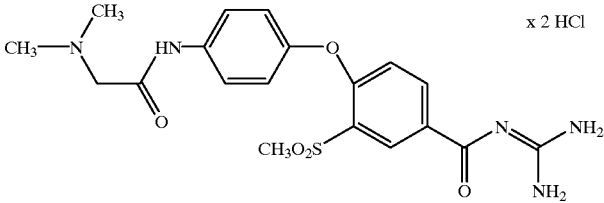

was obtained, in analogy with the protocol described in Variant A, from 4-[4-(N,N-dimethylglycylamino)phenoxy]-3-methylsulfonylbenzoic acid in THF as the reaction medium. Colorless crystalline solid,
m.p.: 223° C.

a) 3-Methylsulfonyl-4-(4-nitrophenoxy)benzoic acid was prepared by reacting 0.02 mol of 3-methylsulfonyl-4-phenoxybenzoic acid with 0.96 ml of 100% nitric acid at −10° C. in a mixture composed of 8 ml of acetic anhydride and 4 ml of glacial acetic acid. After the mixture had been stirred at this temperature for 1.5 hours, it was then stirred at room temperature for 24 hours and at 40° C. for a further 6 hours. It was then poured into ice water and the amorphous, oily product was crystallized with water by stirring. Yellow crystalline substance,
m.p.: 140–150° C.

b) 4-(4-Aminophenoxy)-3-methylsulfonylbenzoic acid was obtained by catalytically hydrogenating 3-methylsulfonyl-4-(4-nitrophenoxy)benzoic acid (Example 37 a) with Raney nickel in methanol under standard pressure until hydrogen uptake was complete. A homogeneous, amorphous oil was obtained after evaporating off the solvent.

c) N,N-Dimethylglycineimidazolide hydrochloride was obtained by reacting N,N-dimethylglycine hydrochloride with carbonyldiimidazole in anhydrous dimethylacetamide, from which the product separated out. The mixture was subjected to further reaction without any additional working-up steps.

d) 4-[4-(N,N-Dimethylglycylamino)phenoxy]-3-methylsulfonylbenzoic acid was obtained by reacting N,N- dimethylglycineimidazolide hydrochloride (Example 37 c) with 4-(4-aminophenoxy)-3-methylsulfonylbenzoic acid (Example 37 b) by means of stirring at room temperature for 5 hours in dimethylacetamide. The solvent was distilled off, the pH was adjusted to 1–2 with HCl and the mixture was extracted with ethyl acetate. The aqueous phase was distilled off and the residue was treated with methanol. After the insoluble material had been filtered off, the desired compound was obtained as a colorless oil.

EXAMPLE 38

4-[4-(N,N-Diethylaminoethyl)aminosulfonylphenoxy]-3 methylsulfonylbenzoylguanidine dihydrochloride

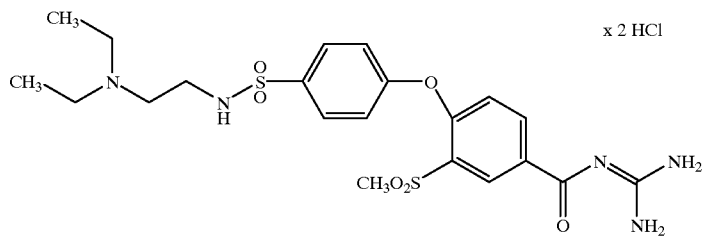

x 2 HCl was obtained, in analogy with the protocol described in Variant A, from 4-[4-(N,N-diethylaminoethyl) aminosulfonylphenoxy]-3-methylsulfonylbenzoic acid in anhydrous dimethylacetamide as the reaction medium. Colorless, crystalline solid, m.p.: 206° C.

a) 4-[4-(N,N-Diethylaminoethyl) aminosulfonylphenoxy]-3-methylsulfonylbenzoic acid was obtained by reacting 0.05 mol of 3-methylsulfonyl-4-(4-chlorosulfonylphenoxy)benzoic acid (Example 33 a) with 0.06 mol of N,N-diethylaminoethylamine in the presence of excess triethylamine (approximately 0.015 mol) in methanol as the reaction medium. After the solvent mixture had been distilled off, the residue was treated with a little water and the mixture was adjusted to pH 4–5. The crystalline precipitate was filtered off.

m.p.: 263–268° C.

EXAMPLE 39

4-[4-(1-Methyl-4-piperazino) sulfonylphenoxy]-3-methylsulfonylbenzoylguanidine dihydrochloride

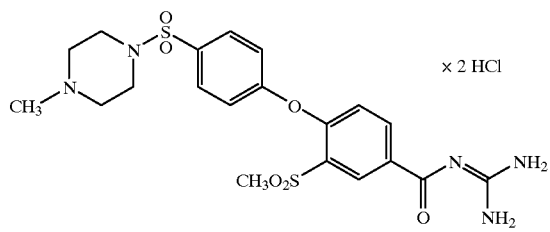

x 2 HCl was obtained, in analogy with the protocol described in Variant A, from 4-[4-(1-methyl-4-piperazino) sulfonylphenoxy]-3-methylsulfonylbenzoic acid in THF as the reaction medium. Colorless crystalline solid, Decomp.: 234–244° C.

a) 4-[4-(1-Methyl-4-piperazino)sulfonylphenoxy]-3-methyl-sulfonylbenzoic acid is obtained by reacting methylsulfonyl-4-(4-chlorosulfonylphenoxy) benzoic acid (Example 33 a) with N-methylpiperazine in analogy with Example 38a).

Colorless crystals,

Decomp.: 287–292° C.

EXAMPLE 40

4-[4-(4-Imidazolylethyl) aminosulfonyl phenoxy]-3-methylsulfonylbenzoylguanidine dihydrochloride

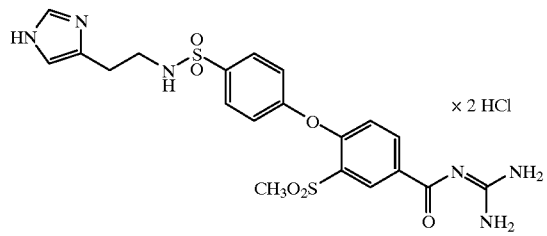

x 2 HCl was obtained, in analogy with the protocol described in Variant A, from 4-[4-(4-imidazolylethyl) aminosulfonylphenoxy]-3-methylsulfonylbenzoic acid in dimethylacetamide as the reaction medium. Colorless crystalline solid, m.p.: 264° C.

a) 4-[4-(4-Imidazolylethyl) aminosulfonylphenoxy]-3-methylsulfonylbenzoic acid was obtained, in analogy with Example 38 a), by reacting methylsulfonyl-4-(4-chlorosulfonylphenoxy)benzoic acid (Example 33 a) with histamine. Colorless, amorphous solid, Decomp. 265° C.

EXAMPLE 41

4-[4-(3-N-Imidazolyl-1-propyl) aminosulfonylphenoxy]-3-methylsulfonylbenzoyl guanidine dihydrochloride

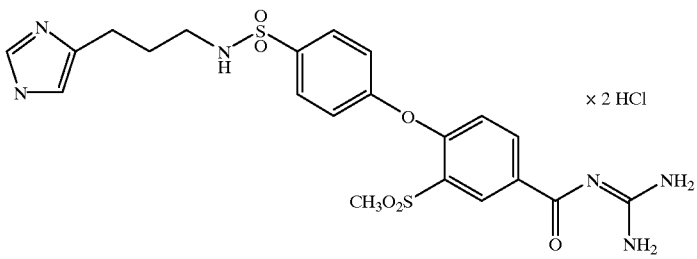

was obtained, in analogy with the protocol described in Variant A, from 4-[4-(3-N-imidazolyl-1-propyl) aminosulfonylphenoxy]-3-methylsulfonylbenzoic acid in THF as the reaction medium. Colorless crystalline solid, Decomp.: 257° C.

a) 4-[4-(3-N-Imidazolyl-1-propyl) aminosulfonylphenoxy]-3-methylsulfonylbenzoic acid was obtained, in analogy with Example 38 a), by reacting methylsulfonyl-4-(4-chloro-sulfonylphenoxy)benzoic acid (Example 33 a) with 1-(3-aminopropyl)imidazole.

Colorless amorphous solid, m.p.: 250° C.

EXAMPLE 42

4-[4-(1-Methyl-2-pyrrolidinylethyl) aminosulfonylphenoxy]-3-methylsulfonylbenzoylguanidine dihydrochloride

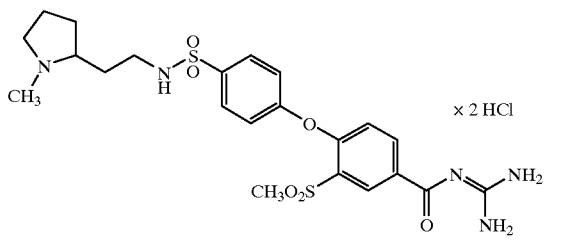

was obtained, in analogy with the protocol described in Variant A, from 4-[4-(1-methyl-2-pyrrolidinylethyl) aminosulfonylphenoxy]-3-methylsulfonylbenzoic acid in dimethylacetamide as the reaction medium. Colorless crystalline solid, m.p.: 254° C.

a) 4-[4-(1-Methyl-2-pyrrolidinylethyl) aminosulfonylphenoxy]-3-methylsulfonylbenzoic acid was obtained, in analogy with Example 38 a), by reacting methylsulfonyl-4-(4-chlorosulfonylphenoxy) benzoic acid (Example 33 a) with 2-(2-aminoethyl)-1-methylpyrrolidine.

m.p. 242–247° C.

EXAMPLE 43

4-[4-(N-Morpholinoethyl) aminosulfonylphenoxy]-3 methylsulfonylbenzoylguanidine dihydrochloride

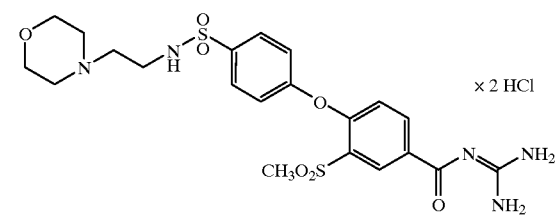

was obtained, in analogy with the protocol described in Variant A, from 4-[4-(N-morpholinoethyl) aminosulfonylphenoxy]-3 methylsulfonylbenzoic acid in dimethyl-acetamide as the reaction medium. Colorless crystalline solid, m.p.: 272° C.

a) 4-[4-(N-Morpholinoethyl) aminosulfonylphenoxy]-3-methylsulfonylbenzoic acid was obtained, in analogy with Example 38 a), by reacting methylsulfonyl-4-(4-chlorosulfonylphenoxy) benzoic acid (Example 33 a) with N-(2-aminoethyl)morpholine. Colorless crystalline compound, m.p. 220–224° C.

EXAMPLE 44

4-[4-N-Piperidinoethyl) aminosulfonylphenoxy]-3 methylsulfonylbenzoylguanidine dihydrochloride

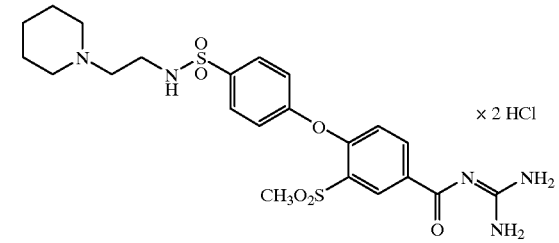

was obtained, in analogy with the protocol described in Variant A, from 4-[4-(N-piperidinoethyl)aminosulfonylphenoxy]-3-methylsulfonylbenzoic acid in anhydrous dimethylacetamide as the reaction medium. Colorless crystalline solid, m.p.: 266° C.

a) 4-[4-(N-Piperidinoethyl) aminosulfonylphenoxy]-3-methylsulfonylbenzoic acid was obtained, in analogy with Example 38 a), by reacting methylsulfonyl-4-(4-chlorosulfonylphenoxy) benzoic acid (Example 33 a) with N-(2-aminoethyl)piperidine.

Colorless crystalline substance,
m.p.: 271–273° C.

EXAMPLE 45
4-[4-(2-Pyridylethyl) aminosulfonylphenoxy]-3-methylsulfonylbenzoylguanidine dihydrochloride

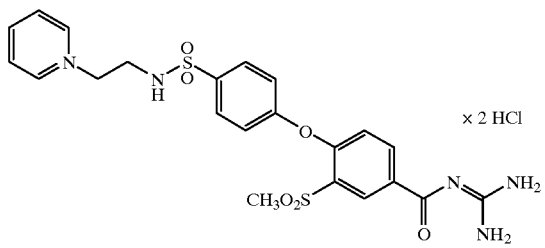

was obtained, in analogy with the protocol described in Variant A, from 4-[4-(2-pyridylethyl) aminosulfonylphenoxy]-3-methylsulfonylbenzoic acid in anhydrous dimethylacetamide as the reaction medium. Colorless crystalline solid,
m.p.: 257° C.

a) 4-[4-(2-Pyridylethyl) aminosulfonylphenoxy)-3-methyl-sulfonylbenzoic acid was obtained, in analogy with Example 38 a), by reacting methylsulfonyl-4-(4-chlorosulfonylphenoxy)benzoic acid (Example 33 a) with 2-(aminoethyl) pyridine. Colorless crystals,
m.p. 268–270° C.

EXAMPLE 46
4-[4-(2-Dimethylamineoethyl), sulfonylmethyl-phenoxy]-3 methylsulfonylbenzoylguanidine dihydrochloride

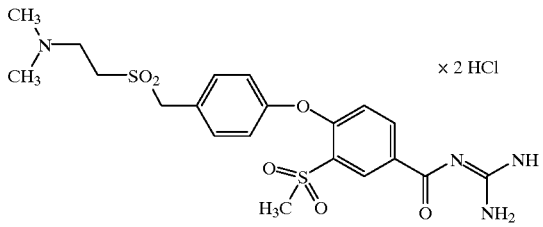

was obtained by peracid oxidation, in analogy with the protocol described in Example "4", from 4-[4-(2-dimethylaminoethyl) thiomethylphenoxy]-3-methyl-sulfonylbenzoylguanidine dihydrochloride (Example 15). Colorless crystals,
m.p.: 245° C.

EXAMPLE 47
4-[4-(2-Dimethylaminoethyl) sulfonylmethylphenoxy]-3-trifluoromethylbenzoylguanidine dihydrochloride

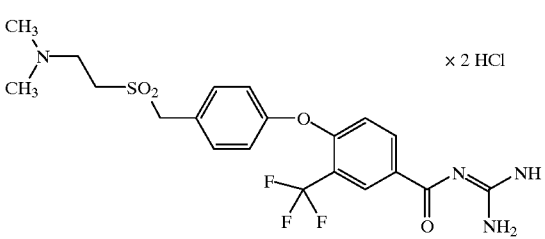

was obtained by peracid oxidation, in analogy with the protocol described in Example 17, from 4-[4-(2-dimethylaminoethyl) thiomethylphenoxy]-3-trifluoromethylbenzoyl guanidine dihydrochloride (Example 19).

Colorless crystals, m.p. 140° C.

Pharmacological data:

Inhibition of the rabbit erythrocyte $Na^+/H^+$ exchanger

New Zealand White rabbits (Ivanovas) were given a standard diet containing 2% cholesterol for six weeks in order to activate $Na^+/H^+$ exchange and thus to render it possible to use flame photometry to determine the influx of $Na^+$ into the erythrocytes via $Na^+/H^+$ exchange. Blood was removed from the aural arteries and rendered incoagulable by adding 25 IU of potassium heparin. A part of each sample was used for determining the hematocrit in duplicate by means of centrifugation. Aliquots of in each case 100 µl were used for measuring the starting content of $Na^+$ in the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris-hydroxymethylaminomethane). After that, the erythrocytes were washed three times with an ice-cold $MgCl_2$/ouabain solution (mmol/l: 112 $MgCl_2$, 0.1 ouabain) and hemolyzed in 2.0 ml of distilled water. The intracellular content of sodium was determined by flame photometry.

The net influx of $Na^+$ was calculated from the difference between the initial sodium values and the sodium content of the erythrocytes following incubation. The amiloride-inhibitable sodium influx was given by the difference in the sodium content of the erythrocytes following incubation with and without $3\times10^{-4}$ mol/l amiloride. The same procedure was followed when using the novel compounds.

Results

Inhibition of the $Na^+/H^+$ exchanger:

| Example | IC50 (µmol/l) |
|---------|---------------|
| 1 | 0.8 |
| 2 | 0.32 |
| 3 | 0.05 |
| 4 | 0.082 |
| 5 | 0.3 |
| 6 | 0.1 |
| 7 | 0.06 |
| 8 | 0.005 |
| 9 | 0.1 |
| 14 | 0.05 |
| 15 | 0.01 |
| 16 | 0.16 |
| 17 | 1 |
| 18 | 0.2 |
| 19 | 0.008 |
| 20 | 0.04 |
| 21 | 0.014 |
| 28 | 0.12 |
| 32 | 0.44 |
| 33 | 0.20 |
| 46 | 0.09 |
| 47 | 0.07 |

EXAMPLE 48
3-Methylsulfonyl-4-(4-(2-t-butoxycarbonylaminoethyl)-phenoxy) benzoylguanidine dihydrochloride

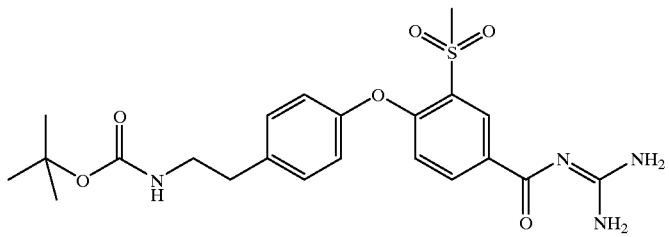

a) Methyl 3-methylsulfonyl-4-(4-(2-t-butoxycarbonylaminoethyl)phenoxy)-benzoate 20.2 g of methyl 4-chloro-3-methylsulfonylbenzoate, 19.3 g of t-butoxycarbonyl-tyramine and 33.8 g of $K_2CO_3$ were stirred at 100° C. for 8 h in 400 ml of NMP. The solvent was removed in vacuo, the residue was taken up using 600 ml of a saturated aqueous $NaHCO_3$ solution and 600 ml of water, and the solution was extracted 3 times with 400 ml of EA each time. The organic phase was dried over $Na_2SO_4$ and the solvent was removed in vacuo. Chromatography on silica gel using DIP yielded 30.4 g of a colorless oil.

| $R_f$ (DIP) = 0.11 | MS (ES): 450 (M + H)⁺ |
|---|---| b) 3-Methylsulfonyl-4-(4-(2-t-butoxycarbonylaminoethyl) phenoxy)-benzoylguanidine, hydrochloride 2.2 g of methyl 3-methylsulfonyl-4-(4-(2-t-butoxycarbonylaminoethyl)phenoxy)benzoate were reacted according to the general procedure for the preparation of benzoylguanidines, variant B, and 1.1 g of the hydrochloride were obtained as colorless crystals, mp 216° C. (with decomposition).

| $R_f$ (EA) = 0.19 | MS (ES): 477 (M + H)⁺ |
|---|---|

EXAMPLE 49
3-Methylsulfonyl-4-(4-(2-aminoethyl)phenoxy)-benzoylguanidine, dihydrochloride

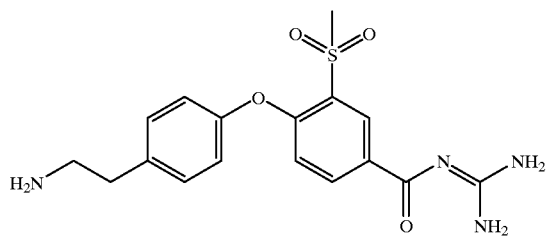

1.1 g of 3-methylsulfonyl-4-(4-(2-t-butoxycarbonylaminoethyl)phenoxy)benzoyl guanidine, hydrochloride were dissolved in 5 ml of trifluoromethanesulfonic acid at 0° C. and the mixture was stirred at this temperature for 2 h, then at RT for 6 h. The reaction mixture was cautiously added to 150 ml of a saturated aqueous $NaHCO_3$ solution and extracted 3 times with 100 ml of EA each time. The organic phase was dried over $Na_2SO_4$ and the solvent was removed in vacuo. Chromatography on silica gel using $CH_2Cl_2$/MeOH/acetone/water 16:8:1:1 yielded 150 mg of a colorless foam, which was converted into the hygroscopic dihydrochloride using a 4 N aqueous HCl solution.

| $R_f$ ($CH_2Cl_2$/MeOH/acetone/water 16:8:1:1) = 0.27 | MS (ES): 377 (M + H)⁺ |
|---|---|

EXAMPLE 50
4-(4-Dimethylaminosulfonyl)phenoxy-5-methylsulfonyl-2-methylbenzoylguanidine

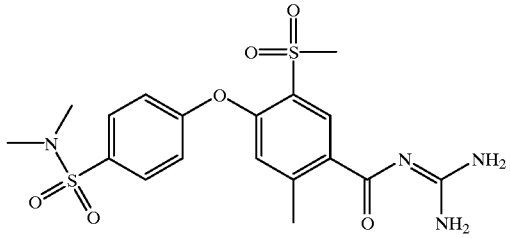

a) 4-Bromo-5-chlorosulfonyl-2-methylbenzoic acid 62 ml of chlorosulfonic acid were slowly added dropwise at RT to 20 g of 4-bromo-2-methylbenzoic acid. The mixture was then stirred at 120° C. for 5 h and, after cooling, cautiously added dropwise to 1.5 kg of ice. The product was filtered off with suction and dried in vacuo. 23 g of white crystals were obtained,
mp 214° C.

| $R_f$ (DIP 2% HOAc) = 0.38 | MS (ES): 249 (M + H)⁺ |
|---|---| b) Methyl 4-bromo-5-methylsulfonyl-2-methylbenzoate 23 g of 4-bromo-5-chlorosulfonyl-2-methylbenzoic acid were added in portions to a warm solution at 70° C. of 14.7 g of $Na_2SO_3$ in 300 ml of water. In the course of this, the pH was kept at pH=9–10 by appropriate addition of 10 N aqueous NaOH solution. The mixture was stirred at 70° C. for 2 h, cooled to RT and adjusted to pH=1 using 6 N aqueous HCl solution and the precipitate was filtered off with suction. The solid was briefly dried, suspended in 100 ml of water and adjusted to pH=10 using 10 N aqueous NaOH solution. The water was removed in vacuo, the residue was suspended in 100 ml of toluene and the solvent was again removed in vacuo. The residue was now suspended in 100 ml of acetone, and the solid was filtered off with suction and dried in vacuo at RT. It was taken up in 200 ml of anhydrous DMF, treated with 16.4 ml of methyl iodide and stirred at 50° C. for 6 h. The reaction mixture was poured onto 2 l of water, stirred for 30 minutes, and the precipitate was filtered off with suction and dried. Recrystallization from a mixture of 300 ml of DIP and 100 ml of EA yielded 18.2 g of a colorless solid, mp 150° C.

| $R_f$ (EA/HEP 1:4) = 0.12 | MS (DCI): 307 (M + H)$^+$ |
|---|---| c) 4-Phenoxy-5-methylsulfonyl-2-methylbenzoic acid 2.5 g of methyl 4-bromo-5-methylsulfonyl-2-methylbenzoate, 0.94 g of phenol and 7.8 g of $Cs_2CO_3$ were dissolved in 40 ml of N-methylpyrrolidone and stirred at 160° C. for 4 h. The reaction mixture was poured onto 100 ml of a saturated aqueous $NaHCO_3$ solution and 100 ml of water and extracted 5 times with 100 ml of EA each time. The aqueous phase was slowly adjusted to pH=2–3 using 6 N aqueous HCl solution and again extracted 5 times with 100 ml of EA each time. The organic phase was dried over $Na_2SO_4$ and the solvent was removed in vacuo. Chromatography on silica gel using DIP/2% HOAc yielded 1.85 g of a colorless solid, mp 195° C.

| $R_f$ (DIP 2% HOAc) = 0.34 | MS (DCI): 307 (M + H)$^+$ |
|---|---| d) 4-(4-Chlorosulfonyl)phenoxy-5-methylsulfonyl-2-methylbenzoyl chloride 1.8 g of 4-phenoxy-5-methylsulfonyl-2-methylbenzoic acid were dissolved in 30 ml of $CHCl_3$ and 4.0 ml of chlorosulfonic acid were added dropwise at RT. The mixture was stirred at RT for 6 h and the solvent and excess chlorosulfonic acid were then removed in vacuo at 40° C. The product was employed without further purification.

e) 4-(4-Dimethylaminosulfonyl)phenoxy-5-methylsulfonyl-2-methylbenzoylguanidine 8.6 g of guanidine hydrochloride were dissolved in 90 ml of DMF and a solution of 9.5 g of potassium t-butoxide in 80 ml of DMF was added dropwise at RT. The mixture was stirred at RT for 90 minutes, then a solution of 3.4 g of 4-(4-chlorosulfonyl)phenoxy-5-methylsulfonyl-2-methylbenzoyl chloride in 40 ml of DMF was added. The reaction mixture was stirred at RT for 24 h and then poured onto 1 l of a saturated aqueous $NaHCO_3$ solution. It was extracted 4 times with 250 ml of EA each time, the organic phase was dried over $Na_2SO_4$ and the solvent was removed in vacuo. Chromatography on silica gel using EA/MeOH 10:1 yielded 49 mg of 4-(4-dimethylaminosulfonyl) phenoxy-5-methylsulfonyl-2-methylbenzoylguanidine as a white crystal mass, mp 163–165° C.

| $R_f$ (EA/MeOH 5:1) = 0.31 | MS (ES): 455 (M + H)$^+$ |
|---|---|

In addition, 120 mg of 4-(4-guanidinosulfonyl)phenoxy-5-methylsulfonyl-2-methylbenzoic acid are obtained as a white foam.

| $R_f$ (EA/MeOH 5:1) = 0.06 | MS (ES): 428 (M + H)$^+$ |
|---|---|

EXAMPLE 51

4-(4-Guanidinosulfonyl)phenoxy-5-methylsulfonyl-2-methyl-benzoylguanidine

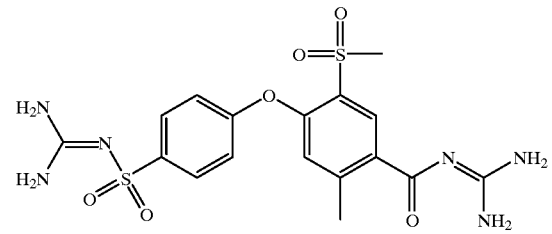

144 mg of potassium t-butoxide were dissolved in 2 ml of DMF, a solution of 135 mg of guanidine hydrochloride in 2 ml of DMF was added at RT and the mixture was stirred for a further 45 minutes.

In addition, 110 mg of 4-(4-guanidinosulfonyl)phenoxy-5-methylsulfonyl-2-methylbenzoic acid were dissolved in 2 ml of DMF, 46 mg of carbonyldiimidazole were added at RT and the mixture was stirred for 30 minutes. The above guanidine solution was then added and the solution was stirred at RT for 24 h. The reaction mixture was poured onto 100 ml of a saturated aqueous $NaHCO_3$ solution and extracted 3 times with 100 ml of EA each time. The organic phase was dried over $Na_2SO_4$ and the solvent was removed in vacuo. 70 mg of a white foam were obtained.

| $R_f$ (EA/MeOH 5:1) = 0.17 | MS (ES): 469 (M + H)$^+$ |
|---|---|

EXAMPLE 52

4-(4-(2-Dimethylaminoethyl)phenoxy)-2-methyl-5-methylsulfonyl-benzoylguanidine dihydrochloride

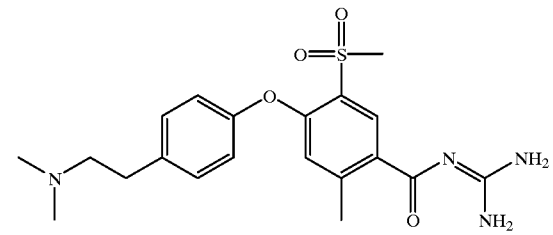

a) Methyl 4-(4-(2-dimethylaminoethyl)phenoxy)-2-methyl-5-methylsulfonylbenzoate 615 mg of methyl 4-bromo-5-methylsulfonyl-2-methylbenzoic acid, 331 mg of 4-(2-dimethylaminoethyl) phenol and 2.0 g of $Cs_2CO_3$ were stirred at 100° C. for 3 h in 10 ml of NMP. The mixture was then poured onto 75 ml of a saturated aqueous $NaHCO_3$ solution, diluted with 75 ml of water and extracted 3 times with 100 ml of EA each time. The organic phase was dried over $Na_2SO_4$, the solvent was removed in vacuo and 680 mg of colorless oil were obtained.

| $R_f$ ($CH_2Cl_2$/MeOH/AcOH/$H_2O$ 16:8:1:1) = 0.69 | MS (ES): 392 (M + H)$^+$ | b) 4-(4-(2-Dimethylaminoethyl)phenoxy)-2-methyl-5-methylsulfonylbenzoylguanidine dihydrochloride 873 mg of guanidine hydrochloride were dissolved in 10 ml of DMF and a solution of 932 mg of potassium t-butoxide in 9 ml of DMF were added at RT. The mixture was stirred at RT for 3 h, then a solution of 650 mg of methyl 4-(4-(2-dimethylaminoethyl)phenoxy)-2-methyl-5-methylsulfonylbenzoate in 10 ml of DMF was added and the mixture was stirred at RT for 12 h. The reaction mixture was poured onto 250 ml of water and 50 ml of a saturated aqueous $NaHCO_3$ solution and the mixture was extracted 3 times using 100 ml of EA each time. The organic phase was dried over $Na_2SO_4$ and the solvent was removed in vacuo and 510 mg of a viscous oil were obtained. This was dissolved in 15 ml of acetone, 4 ml of a 4 N aqueous HCl solution were added and the volatile components were removed in vacuo. 530 mg of white crystals were obtained, mp 260° C. (with decomposition).

| $R_f$ ($CH_2Cl_2$/MeOH/AcOH/$H_2O$ 16:8:1:1) = 0.25 | MS (ES): 419 (M + H)$^+$ |

EXAMPLE 53

4-(4-Guanidinosulfonyl)phenoxy-2-methyl-5-trifluoromethylbenzoylguanidine

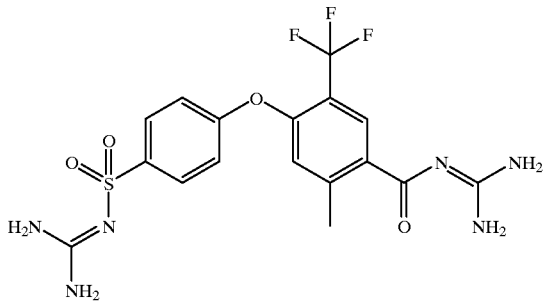

a) 4-Bromo-2-methyl-5-nitrobenzoic acid 11 g of 4-bromo-2-methylbenzoic acid were dissolved in 70 ml of 96% sulfuric acid and 70 ml of 65% nitric acid were added dropwise at 0° C. and the mixture was stirred at 0° C. for 3 h. The mixture was then poured onto 500 g of ice, stirred for 1 h, and the product was filtered off with suction and dried in vacuo. 14.4 g of white crystals were obtained, mp 162° C.

Beside the desired regioisomers, approximately a further 20% of 4-bromo-2-methyl-3-nitrobenzoic acid can be detected by NMR spectroscopy.

b) Methyl 4-bromo-2-methyl-5-nitrobenzoate 14.3 g of 4-bromo-2-methyl-5-nitrobenzoic acid were dissolved in 250 ml of MeOH and 11.6 g of $SOCl_2$ were slowly added dropwise. The mixture was allowed to stand at RT for 5 days, the volatile components were removed in vacuo and the residue is recrystallized from DIP. 5.2 g of white crystals were obtained, mp 104° C.

| $R_f$ (EA/HEP 1:4) = 0.26 | MS (DCI): 274 (M + H)$^+$ | c) Methyl 2-methyl-5-nitro-4-phenylbenzoate 22.6 g of methyl 4-bromo-2-methyl-5-nitrobenzoate, 23 g of $K_2CO_3$ and 7.8 g of phenol were stirred at 120° C. for 2 hours in 300 ml of DMF. The solvent was removed in vacuo, 2 l of water were added, and the mixture was adjusted to pH=7 using aqueous HCl solution and extracted 3 times using 500 ml of EA each time. The organic phase was dried over $Na_2SO_4$, the solvent was removed in vacuo and chromatography on silica gel using EA/HEP 1:4 yielded 13 g of a colorless oil.

| $R_f$ (EA/HEP 1:4) = 0.18 | MS (DCI): 288 (M + H)$^+$ | d) Methyl 5-amino-2-methyl-4-phenylbenzoate 13 g of methyl 2-methyl-5-nitro-4-phenylbenzoate were dissolved in 150 ml of MeOH and treated with 10 g of iron powder. A saturated aqueous HCl solution was then slowly added dropwise and the mixture was stirred at RT for 2 hours. The volatile components are removed in vacuo at a maximum temperature of 30° C., 500 ml of a saturated aqueous $Na_2CO_3$ solution were added, the iron salts were filtered off and the filtrate was extracted 3 times using 500 ml of EA each time. The organic phase was dried over $Na_2SO_4$ and the solvent was removed in vacuo. 10 g of colorless oil were obtained.

| $R_f$ (DIP) = 0.50 | MS (DCI): 258 (M + H)$^+$ | e) Methyl 5-iodo-2-methyl-4-phenylbenzoate 10 g of methyl 5-amino-2-methyl-4-phenylbenzoate are suspended at 0° C. in 200 ml of a half-concentrated aqueous sulfuric acid solution and a solution of 2.95 g of $NaNO_2$ in 50 ml of water was slowly added dropwise at 5° C. The mixture was stirred at 0 to 5° C. for 15 minutes, then this suspension was poured in portions into a warm solution at 50° C. of 65 g of NaI in 300 ml of water. The mixture was extracted 3 times using 300 ml of EA each time, the organic phase was dried over $Na_2SO_4$ and the solvent was removed in vacuo. Chromatography on silica gel using EA/HEP 1:4 yielded 5.8 g of a pale yellow oil.

| $R_f$ (EA/HEP 1:4) = 0.39 | MS (DCI): 369 (M + H)$^+$ | f) Methyl 2-methyl-4-phenyl-5-trifluoromethylbenzoate 5.8 g of methyl 5-iodo-2-methyl-4-phenylbenzoate, 4.8 g of potassium trifluoroacetate and 6.6 g of CuI were added to 300 ml of toluene and 100 ml of DMF and the toluene was distilled out of the reaction mixture at a bath temperature of 160° C. The DMF solution freed from traces of water in this way was then refluxed for 8 h.

4.8 g of potassium trifluoroacetate and 6.6 g of CuI and also 100 ml of toluene were added again, the toluene was distilled off and the mixture was refluxed for 4 hours. The reaction mixture was added to 500 ml of water and extracted 3 times using 200 ml of EA each time. Chromatography on silica gel using EA/HEP 1:8 yielded 2.66 g of a colorless oil.

| $R_f$ (EA/HEP 1:8) = 0.25 | MS (DCI): 311 (M + H)$^+$ |
|---|---| g) 2-Methyl-4-phenyl-5-trifluoromethylbenzoic acid 2.6 g of methyl 2-methyl-4-phenyl-5-trifluoromethylbenzoate were dissolved in 100 ml of MeOH, 20 ml of a 1 N aqueous NaOH solution were added and the solution was stirred at RT for 8 h. The reaction mixture was poured onto 100 ml of a saturated aqueous NaHSO$_4$ solution and extracted 3 times using 100 ml of EA each time. The organic phase was dried over Na$_2$SO$_4$ and the solvent was removed in vacuo.

1.93 g of a viscous oil are obtained.

| $R_f$ (EA) = 0.08 | MS (DCI): 297 (M + H)$^+$ |
|---|---| h) 4-(4-Chlorosulfonyl)phenyl-2-methyl-5-trifluoromethylbenzoic acid 1.0 g of 2-methyl-4-phenyl-5-trifluoromethylbenzoic acid was dissolved in 50 ml of CH$_2$Cl$_2$ and 1.1 ml of chlorosulfonic acid were slowly added dropwise at RT. The mixture was stirred at RT for 1 hour, added to 100 g of ice, and the product was filtered off with suction and dried in vacuo. 1.1 g of a colorless solid were obtained, which is directly employed further.

i) 4-(4-Chlorosulfonyl)phenyl-2-methyl-5-trifluoromethylbenzoyl chloride 1.1 g of 4-(4-chlorosulfonyl)phenyl-2-methyl-5-trifluoromethylbenzoic acid were dissolved in 15 ml of SOCl$_2$ and 0.4 ml of DMF was added. The mixture was refluxed for 5 h and the volatile components were then removed in vacuo. 1.1 g of a viscous oil were obtained, which is directly employed further.

j) 4-(4-Guanidinosulfonyl)phenoxy-2-methyl-5-trifluoromethylbenzoylguanidine 3.4 g of guanidine hydrochloride were dissolved in 100 ml of DMF, 3.3 g of potassium t-butoxide were added and the mixture was stirred at RT for 1 h. A solution of 1.1 g of 4-(4-chlorosulfonyl)phenyl-2-methyl-5-trifluoromethyl-benzoyl chloride in 50 ml of DMF was added dropwise to this solution. The mixture was stirred at RT for 90 minutes and allowed to stand for 18 h. The solvent was removed in vacuo, the residue was taken up using 100 ml of water and the solution was extracted 3 times using 100 ml of EA each time. The organic phase was dried over Na$_2$SO$_4$ and the solvent was removed in vacuo. Chromatography on silica gel using EA/MeOH 5:1 yielded 354 mg of colorless crystals,
mp 160–164° C. (with decomposition).

| $R_f$ (EA/MeOH 5:1) = 0.26 | MS (ES): 459 (M + H)$^+$ |
|---|---|

EXAMPLE 54

2-Chloro-4-(4-(2-dimethylaminoethyl)phenoxy)-5-methylsulfonylbenzoylguanidine

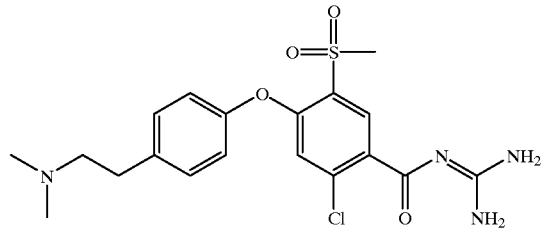

a) 2-Chloro-5-chlorosulfonyl-4-fluorobenzoic acid 17.5 g of 2-chloro-4-fluorobenzoic acid were added in portions to 67 ml of chlorosulfonic acid and the mixture was stirred at 95° C. for 10 h. The reaction mixture was slowly added dropwise to 600 g of ice, and the precipitate was filtered off with suction, washed 3 times with 200 ml of water each time and dried in vacuo.

20.3 g of a colorless solid were obtained,
mp 137° C.

| $R_f$ (DIP/2% HOAc) = 0.44 | MS (DCI): 273 (M + H)$^+$ |
|---|---| b) Methyl 2-chloro-4-fluoro-5-methylsulfonylbenzoate 11.6 g of Na$_2$SO$_3$ are dissolved in 44 ml of water and 20.1 g of 2-chloro-5-chlorosulfonyl-4-fluorobenzoic acid were added in portions at 70° C. and at the same time the pH was kept between 9 and 10 by dropwise addition of 10 N aqueous NaOH solution. The reaction mixture was stirred at 70° C. for 2.5 hours, poured into 300 ml of a 6 N aqueous HCl solution and the precipitate was filtered off with suction. It was washed 3 times with 50 ml of water each time and the aqueous phase was extracted 3 times using 200 ml of EA each time. The organic phase was dried over Na$_2$SO$_4$, the solvent was removed in vacuo and the residue was combined with the precipitate and 14.6 g of carboxysulfinic acid were obtained. This was taken up using 61 ml of a 2 N aqueous NaOH solution and the water was removed in vacuo and 20.9 g of the disodium salt were obtained. This was suspended in 150 ml of DMF, 16.2 ml of methyl iodide were added and the mixture was stirred at 60° C. for 3 hours. The reaction mixture was poured onto 800 ml of a 2 N aqueous HCl solution and extracted 6 times using 200 ml of EA each time. The organic phase was washed a further 2 times using 400 ml of a saturated aqueous NaHCO$_3$ solution each time, dried over Na$_2$SO$_4$ and the solvent was removed in vacuo. Chromatography on silica gel using EA/HEP 1:4 yielded 12.0 g of a colorless solid,
mp 139° C.

| $R_f$ (EA/HEP 1:1) = 0.40 | MS (DCI): 267 (M + H)$^+$ |
|---|---| c) Methyl 2-chloro-4-(4-(2-dimethylaminoethyl)phenoxy)-5-methylsulfonyl-benzoate 534 mg of methyl 2-chloro-4-fluoro-5-methylsulfonylbenzoate, 331 mg of 4-(2-dimethylaminoethyl)phenol and 2.0 g of Cs$_2$CO$_3$ were dissolved in 10 ml of NMP and the mixture was stirred at 100° C. for 3 hours. The reaction mixture was poured onto 150 ml of a saturated aqueous NaHCO$_3$ solution and extracted 3 times using 100 ml of EA each time. The organic phase was dried over Na$_2$SO$_4$ and the solvent was removed in vacuo. Chromatography on silica gel using EA/MeOH 3:1 yields 240 mg of a viscous oil.

| R$_f$ (EA/MeOH 3:1) = 0.11 | MS (ESI): 412 (M + H)$^+$ |
| --- | --- | d) 2-Chloro-4-(4-(2-dimethylaminoethyl)phenoxy)-5-methylsulfonylbenzoyl-guanidine 268 mg of guanidine hydrochloride were dissolved in 3 ml of DMF and a solution of 286 mg of potassium t-butoxide in 3 ml of DMF is added. The mixture was stirred at RT for 3 hours, then a solution of 210 mg of methyl 2-chloro-4-(4-(2-dimethylaminoethyl)phenoxy)-5-methylsulfonylbenzoate in 4 ml of DMF was added. The mixture was stirred at RT for 3 hours and allowed to stand at RT for 18 hours. The mixture was poured onto 150 ml of water and extracted 3 times using 100 ml of EA each time. The organic phase was dried over Na$_2$SO$_4$ and the solvent was removed in vacuo. 230 mg of a glassy solid were obtained.

| R$_f$ (CH$_2$Cl$_2$/MeOH/H$_2$O/AcOH 16:8:1:1) = 0.53 | MS (ESI): 439 (M + H)$^+$ |
| --- | --- |

EXAMPLE 55

2-Chloro-4-(4-(2-dimethylaminoethyl)phenoxy)-5-trifluoro-methylbenzoylguanidine

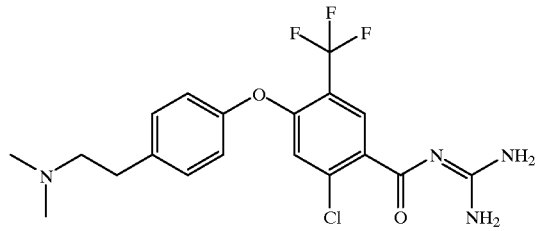

and

EXAMPLE 56

2-Chloro-4-(4-(2-dimethylaminoethyl)phenoxy)-5-iodobenzoylguanidine

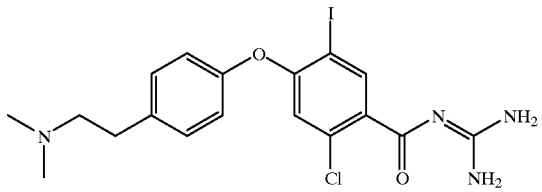

a) 2-Chloro-4-fluoro-5-iodobenzoic acid 17.5 g of 2-chloro-4-fluorobenzoic acid were dissolved in 50 ml of trifluoromethanesulfonic acid and 22.5 g of N-iodosuccinimide were added in portions at 0° C. The mixture was stirred at 0° C. for 1 hour, then at RT for a further hour. 4.5 g of N-iodosuccinimide were added and the mixture was stirred at RT for a further 2.5 hours. The reaction mixture was added to 400 g of ice, stirred for 30 minutes and the product was filtered off with suction. It was washed 2 times using 200 ml of water each time and dried in vacuo. 30.8 g of a colorless solid were obtained.

| R$_f$ (EA/MeOH 5:1) = 0.71 | MS (DCI): 301 (M + H)$^+$ |
| --- | --- | b) Methyl 2-chloro-4-fluoro-5-iodobenzoate 30.8 g of 2-chloro-4-fluoro-5-iodobenzoic acid were dissolved in 300 ml of MeOH and 36 ml of thionyl chloride were added dropwise. The mixture was refluxed for 4 hours and the volatile constituents were removed in vacuo. The residue was taken up using 600 ml of EA and washed with 400 ml of a half-concentrated aqueous Na$_2$CO$_3$ solution. The organic phase was dried over Na$_2$SO$_4$ and the solvent was removed in vacuo. The residue was stirred with 200 ml of HEP, and the precipitate was filtered off and washed with 100 ml of HEP. 5.8 g of methyl 2-chloro-4-fluoro-3,5-diiodobenzoate were obtained, mp 155° C.

| R$_f$ (EA/HEP 1:4) = 0.41 | MS (DCI): 441 (M + H)$^+$ |
| --- | --- |

The solvent was removed in vacuo from the filtrate containing the desired product and 23.5 g of white crystals were obtained, mp 52° C.

| R$_f$ (EA/HEP 1:4) = 0.47 | MS (DCI): 315 (M + H)$^+$ |
| --- | --- | c) Methyl 2-chloro-4-fluoro-5-trifluoromethylbenzoate 12.5 g of methyl 2-chloro-4-fluoro-5-iodobenzoate, 11.2 g of potassium trifluoroacetate and 15.6 g of CuI were suspended in 320 ml of DMF and 240 ml of toluene and the toluene was distilled off to remove traces of water. The reaction mixture was refluxed for 2 hours, then poured onto 1 l of a half-concentrated aqueous NaHCO$_3$ solution and extracted 4 times using 350 ml of EA each time. The organic phase was dried over Na$_2$SO$_4$ and the solvent was removed in vacuo. Chromatography on silica gel using EA/HEP 1:8 yielded 860 mg of a viscous oil. Contains an inseparable amount of methyl 2-chloro-4-fluoro-5-iodobenzoate.

| R$_f$ (EA/HEP 1:8) = 0.35 | MS (DCI): 257 (M + H)$^+$ |
| --- | --- | d) Methyl 2-chloro-4-(4-(2-dimethylaminoethyl)phenoxy)-5-trifluoromethyl-benzoate 860 mg of methyl 2-chloro-4-fluoro-5-trifluoromethylbenzoate, 554 mg of 4-(2-dimethylaminoethyl)phenol and 3.3 g of Cs$_2$CO$_3$ were dissolved in 15 ml of NMP and the mixture was stirred at 60° C. for 90 minutes. The reaction mixture was poured onto 250 ml of a half-concentrated aqueous NaHCO$_3$ solution and extracted 3 times using 150 ml of EA each time. The organic phase was dried over Na$_2$SO$_4$ and the solvent was removed in vacuo. Chromatography on silica gel using EA/MeOH 3:1 yielded 880 mg of a viscous oil. Contains an inseparable amount of methyl 2-chloro-4-(4-(2-dimethylaminoethyl)phenoxy)-5-iodobenzoate.

| $R_f$ (EA/MeOH 3:1) = 0.14 | MS (ESI): 402 (M + H)⁺ | e) 2-Chloro-4-(4-(2-dimethylaminoethyl)phenoxy)-5-trifluoromethylbenzoylguanidine 1.1 g of guanidine hydrochloride were dissolved in 10 ml of DMF and a solution of 1.2 g of potassium t-butoxide in 10 ml of DMF is added. The mixture was stirred at RT for 2 hours, then a solution of methyl 2-chloro-4-(4-(2-dimethylaminoethyl)phenoxy)-5-trifluoromethylbenzoate in 10 ml of DMF was added and the mixture was stirred at RT for 4 hours. The reaction mixture was poured onto 250 ml of water and the product was filtered off. Chromatography of the precipitate on silica gel using acetone/MeOH 20:1+2% triethylamine yielded 130 mg of the title compound as white crystals,
mp 141° C.

| $R_f$ (acetone/MeOH 15:1 + 2% triethylamine) = 0.28 | MS (ESI): 429 (M + H)⁺ |

In addition, 390 mg of Example 55 are obtained: 2-chloro-4-(4-(2-dimethylaminoethyl)phenoxy)-5-iodo-benzoylguanidine, white crystals,
mp 150° C.

| $R_f$ (acetone/MeOH 15:1 + 2% triethylamine) = 0.23 | MS (ESI): 487 (M + H)⁺ |

EXAMPLE 57
2-Chloro-4-(4-guanidinosulfonyl)phenoxy-5-methylsulfonylbenzoylguanidine

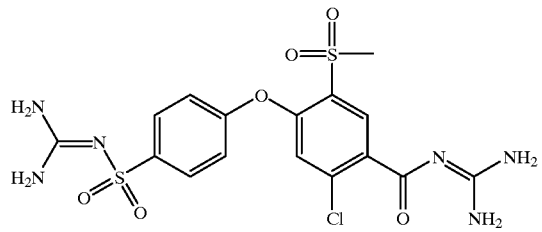

and

EXAMPLE 58
2-Dimethylamino-4-(4-guanidinosulfonyl)phenoxy-5-methylsulfonylbenzoylguanidine

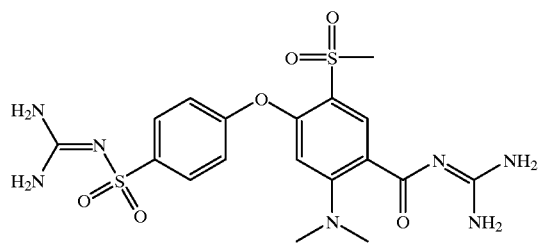

and

EXAMPLE 59
2-Dimethylamino-4-(4-dimethylaminosulfonyl)phenoxy-5-methylsulfonylbenzoylguanidine

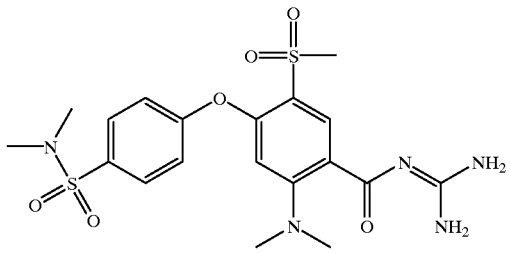

and

EXAMPLE 60
2-Chloro-4-(4-dimethylaminosulfonyl)phenoxy-5-methylsulfonylbenzoylguanidine

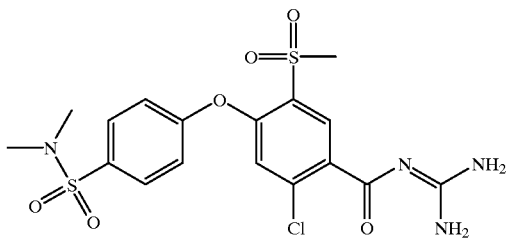

a) Methyl 2-chloro-4-phenoxy-5-methylsulfonylbenzoate
2.7 g of methyl 2-chloro-4-fluoro-5-methylsulfonylbenzoate (Example 54 b), 1.2 g of phenol and 4.1 g of $K_2CO_3$ were stirred at 60° C. for 75 minutes in 30 ml of NMP. The reaction mixture was poured onto 300 ml of water and extracted 3 times using 200 ml of EA each time. The organic phase was washed a further 2 times using 150 ml of water each time, dried over $Na_2SO_4$ and the solvent was removed in vacuo. 3.4 g of a colorless oil were obtained.

| $R_f$ (EA/toluene 1:2) = 0.71 | MS (DCI): 341 (M + H)⁺ | b) 2-Chloro-4-phenoxy-5-methylsulfonylbenzoic acid
3.4 g of methyl 2-chloro-4-phenoxy-5-methylsulfonylbenzoate were dissolved in 40 ml of MeOH and 9.9 ml of a 2 N aqueous NaOH solution were added. The mixture was stirred at RT for 4 hours, adjusted to pH=1–2 using a 2 N aqueous HCl solution and extracted 3 times using 150 ml of EA each time. The organic phase was dried over $Na_2SO_4$, the solvent was removed in vacuo and 2.9 g of white crystals were obtained,
mp 200° C.

| $R_f$ (EA) = 0.17 | MS (DCI): 327 (M + H)⁺ | c) 2-Chloro-4-(4-chlorosulfonyl)phenoxy-5-methylsulfonylbenzoic acid
2.9 g of 2-chloro-4-phenoxy-5-methylsulfonylbenzoic acid were dissolved in 44 ml of $CHCl_3$, 5.9 ml of chlorosulfonic acid were added dropwise and the mixture was stirred at RT for 2 hours. The reaction mixture was poured onto 300 g of ice and extracted 3 times using 150 ml of EA each time. The organic phase was dried over Na$_2$SO$_4$ and the solvent was removed in vacuo. 3.1 g of an amorphous solid were obtained.

| R$_f$ (DIP 2% HOAc) = 0.06 | MS (ESI): 425 (M + H)$^+$ |
|---|---| d) 2-Chloro-4-(4-chlorosulfonyl)phenoxy-5-methylsulfonylbenzoyl chloride 3.0 g of 2-chloro-4-(4-chlorosulfonyl)phenoxy-5-methylsulfonylbenzoic acid were treated with 36 ml of SOCl$_2$ and refluxed for 4 hours and 20 minutes. The volatile constituents were removed in vacuo and 3.2 g of a viscous oil were obtained which was directly reacted further.

e) 2-Chloro-4-(4-guanidinosulfonyl)phenoxy-5-methylsulfonylbenzoylguanidine and 2-dimethylamino-4-(4-guanidinosulfonyl)phenoxy-5-methylsulfonylbenzoylguanidine and 2-dimethylamino-4-(4-dimethylaminosulfonyl)phenoxy-5-methylsulfonyl-benzoylguanidine and 2-chloro-4-(4-dimethylaminosulfonyl)phenoxy-5-methylsulfonylbenzoylguanidine 7.5 g guanidine hydrochloride were dissolved in 80 ml of DMF and a solution of 8.0 g of potassium t-butoxide in 70 ml of DMF was added at RT. The mixture was stirred at RT for 1 hour, then a solution of 3.2 g of 2-chloro-4-(4-chlorosulfonyl)phenoxy-5-methylsulfonylbenzoyl chloride in 40 ml of DMF was added dropwise, and the mixture was stirred at RT for 12 hours and allowed to stand overnight. The reaction mixture was poured onto 1 l of water and extracted 6 times using 200 ml of EA each time. The organic phase was dried over Na$_2$SO$_4$, the solvent was removed in vacuo and 1.8 g of a crude mixture of the 4 title compounds were obtained. Chromatography on silica gel using a gradient of EA/MeOH 10:1 to EA/MeOH 1:1 yielded 350 mg of 2-chloro-4-(4-guanidinosulfonyl)phenoxy-5-methylsulfonyl-benzoylguanidine, mp 95–97° C.

| R$_f$ (EA/MeOH 3:1) = 0.11 | MS (ESI): 489 (M + H)$^+$ |
|---|---|

90 mg of 2-dimethylamino-4-(4-guanidinosulfonyl)phenoxy-5-methylsulfonylbenzoylguanidine, mp 127–128° C.

| R$_f$ (EA/MeOH 1:1) = 0.10 | MS (ESI): 498 (M + H)$^+$ |
|---|---|

170 mg of 2-dimethylamino-4-(4-dimethylaminosulfonyl)phenoxy-5-methylsulfonylbenzoylguanidine, mp 150–151° C.

| R$_f$ (EA/MeOH 3:1) = 0.06 | MS (ESI): 484 (M + H)$^+$ |
|---|---|

40 mg of 2-chloro-4-(4-dimethylaminosulfonyl)phenoxy-5-methylsulfonylbenzoylguanidine, amorphous

| R$_f$ (EA/MeOH 3:1) = 0.36 | MS (ESI): 475 (M + H)$^+$ |
|---|---|

EXAMPLE 61

4-(4-(2-t-Butoxycarbonylaminoethyl)phenoxy-2-methyl-5-methylsulfonylbenzoylguanidine

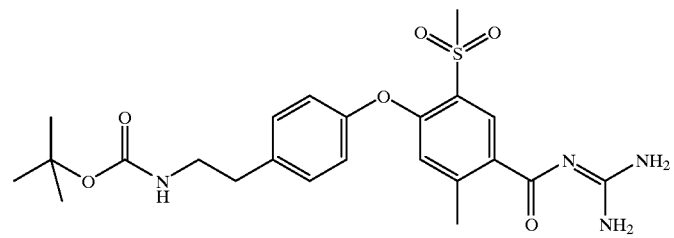

a) Methyl 4-(4-(2-t-butoxycarbonylaminoethyl)phenoxy-2-methyl-5-methylsulfonylbenzoate 2.4 g of t-butoxycarbonyltyramine, 3.1 g of 4-bromo-5-methylsulfonyl-2-methylbenzoate (Example 50 b) and 4.2 g of K$_2$CO$_3$ were stirred at 100° C. for 26 h in 45 ml of NMP. The reaction mixture was diluted with 400 ml of a half-concentrated aqueous NaHCO$_3$ solution and extracted 4 times using 125 ml of EA each time. The organic phase was dried over Na$_2$SO$_4$ and the solvent was removed in vacuo. Chromatography on silica gel with DIP yielded 3.4 g of white crystals, mp 130° C.

| R$_f$ (DIP) = 0.12 | MS (ESI): 464 (M + H)$^+$ | b) 4-(4-(2-t-Butoxycarbonylaminoethyl)phenoxy-2-methyl-5-methylsulfonylbenzoylguanidine 3.8 g of guanidine hydrochloride were dissolved in 40 ml of DMF and a solution of 4.1 g of potassium t-butoxide in 36 ml of DMF was added at RT. The solution was stirred at RT for 75 minutes, then this solution was added dropwise to a solution of 3.4 g of methyl 4-(4-(2-t-butoxycarbonylaminoethyl)phenoxy-2-methyl-5-methylsulfonylbenzoate in 36 ml of DMF. The mixture was stirred at RT for 6 hours and allowed to stand overnight. The reaction mixture was poured into 500 ml of a half-concentrated aqueous NaHCO$_3$ solution and extracted 5 times using 150 ml of EA each time. The organic phase was then washed a further 2 times with 200 ml of a half-concentrated aqueous NaHCO$_3$ solution each time, was dried over Na$_2$SO$_4$ and the solvent was removed in vacuo. The residue is recrystallized from EA and 530 mg of white crystals were obtained, mp 205° C. The solvent was removed in vacuo from the mother liquor, the residue was chromatographed on silica gel using EA/MeOH 10:1 and 2.31 g of an amorphous foam were obtained, which did not differ from the crystalline fraction by thin-layer chromatography.

| R$_f$ (EA/MeOH 10:1) = 0.30 | MS (FAB): 491 (M + H)$^+$ |

EXAMPLE 62

4-(4-(2-Aminoethyl)phenoxy-2-methyl-5-methylsulfonylbenzoylguanidine

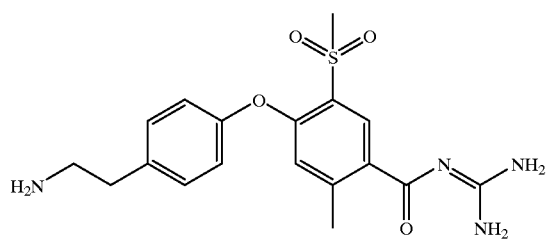

2.3 g of 4-(4-(2-t-butoxycarbonylaminoethyl)phenoxy-2-methyl-5-methylsulfonylbenzoylguanidine were dissolved in 12 ml of CF$_3$SO$_3$H at 0° C. and the mixture was stirred at this temperature for 150 minutes. The reaction mixture was added dropwise to 400 ml of an ice-cooled, saturated aqueous Na$_2$CO$_3$ solution and extracted 10 times using 200 ml of EA each time. The organic phase was dried over Na$_2$SO$_4$ and the solvent was removed in vacuo. Chromatography on silica gel using CH$_2$Cl$_2$/MeOH/AcOH/H$_2$O 32:8:1:1 yielded 110 mg of an amorphous solid.

| R$_f$ (acetone/MeOH/15:1, 2% triethylamine) = 0.37 | MS (ESI): 391 (M + H)$^+$ |

EXAMPLE 63

4-(4-(2-Acetylaminoethyl)phenoxy-3-methylsulfonylbenzoylguanidine

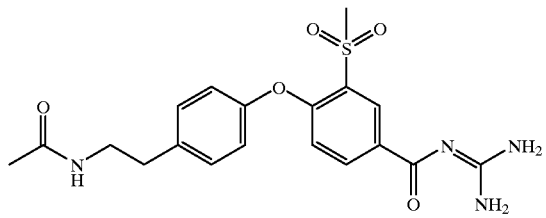

a) Methyl 4-(4-(2-acetylaminoethyl)phenoxy-3-methylsulfonylbenzoate 2.3 g of methyl 3-methylsulfonyl-4-(4-(2-t-butoxycarbonylaminoethyl)phenoxy) benzoate were dissolved in 30 ml of CH$_2$Cl$_2$ and 35 ml of trifluoroacetic acid were added. The mixture was stirred at RT for 90 minutes and allowed to stand overnight. The reaction mixture was poured onto 150 ml of a saturated aqueous Na$_2$CO$_3$ solution and extracted 3 times using 100 ml of EA each time. The organic phase was dried over Na$_2$SO$_4$ and the solvent was removed in vacuo. The residue was taken up using 35 ml of triethylamine and 1.1 ml of acetyl chloride were added dropwise at RT. The mixture was stirred at RT for 90 minutes, allowed to stand overnight and finally refluxed for 45 minutes. The reaction mixture was poured onto 150 ml of a saturated aqueous NaHCO$_3$ solution and extracted 3 times using 100 ml of EA each time. The organic phase was dried over Na$_2$SO$_4$, the solvent was removed in vacuo and the residue was chromatographed on silica gel using EA. 770 mg of a colorless solid were obtained, mp 151° C.

| R$_f$ (EA) = 0.12 | MS (ESI): 392 (M + H)$^+$ | b) 4-(4-(2-Acetylaminoethyl)phenoxy-3-methylsulfonylbenzoylguanidine 740 mg of methyl 4-(4-(2-acetylaminoethyl)phenoxy-3-methylsulfonyl benzoate were guanylated according to the general working procedure for the synthesis of benzoylguanidines, variant B and 540 mg of an amorphous solid were obtained, mp (hydrochloride) 215–216° C.

| R$_f$ (EA) = 0.025 | MS (ESI): 419 (M + H)$^+$ |

The title compounds of Examples 64 and 65 were synthesized analogously to Example 63:

EXAMPLE 64

4-(4-(2-Benzoylaminoethyl)phenoxy-3-methylsulfonyl-benzoylguanidine

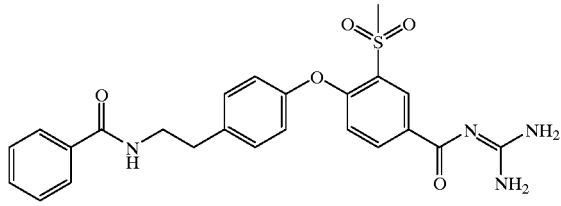

mp (hydrochloride) > 266° C.  MS(ESI): 481(M + H)⁺
R_f (EA) = 0.06

EXAMPLE 65

3-Methylsulfonyl-4-(4-(2-(3-phenylpropionyl)aminoethyl)phenoxy-benzoylguanidine

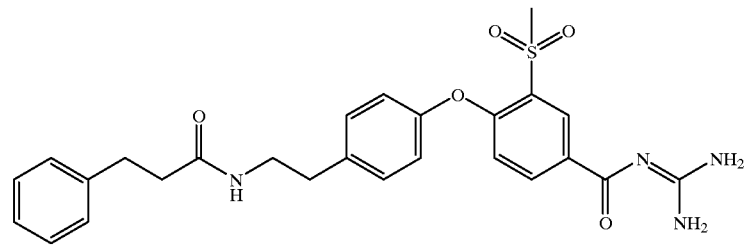

mp (hydrochloride) 266° C.  MS(ESI): 509(M + H)⁺
R_f (EA) = 0.036

EXAMPLE 66

4-(4-(2-Acetylaminoethyl)phenoxy-2-methyl-5-methylsulfonylbenzoylguanidine

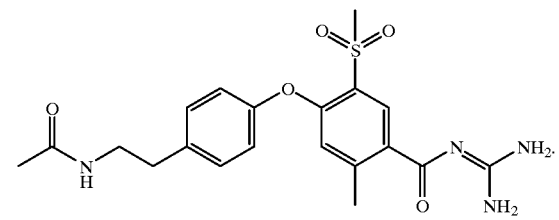

a) Methyl 4-(4-(2-acetylaminoethyl)phenoxy-2-methyl-5-methylsulfonyl-benzoate 1.5 g of methyl 4-bromo-5-methylsulfonyl-2-methylbenzoate, 0.9 g of Boc-tyramine and 2.1 g of $K_2CO_3$ were stirred at 100° C. for 9 hours in 25 ml of NMP. The reaction mixture was poured onto 300 ml of a half-concentrated aqueous $NaHCO_3$ solution, extracted 4 times using 200 ml of EA each time and washed 3 times with 150 ml of water. The organic phase was dried over $Na_2SO_4$, the solvent was removed in vacuo and the residue was chromatographed on silica gel using EA. 1.5 g of a colorless solid were obtained, mp 151° C.

| R_f (EA) = 0.19 | MS (ESI): 406 (M + H)⁺ | b) 4-(4-(2-Acetylaminoethyl)phenoxy-2-methyl-5-methylsulfonyl-benzoylguanidine 1.1 g of guanidine hydrochloride were dissolved in 11 ml of DMF and a solution of 1.1 g of potassium t-butoxide in 10 ml of DMF was added at RT. The mixture was stirred at RT for 75 minutes, then a solution of 0.8 g of methyl 4-(4-(2-acetylaminoethyl)phenoxy-2-methyl-5-methylsulfonyl-benzoate in 10 ml of DMF were added, and the mixture was stirred at RT for 10 hours and allowed to stand overnight. The reaction mixture was poured onto 200 ml of water, and the precipitate was filtered off and dried. 640 mg of a colorless solid were obtained, mp 150° C.

| R_f (EA/MeOH 5:1) = 0.13 | MS (ESI): 433 (M + H)⁺ |

Inhibition of the $Na^+/H^+$ exchanger.

| Example | IC50 (mmol/l) |
|---------|---------------|
| 48 | 0.07 |
| 49 | 0.2 |
| 50 | 0.09 |
| 51 | <0.2 |
| 52 | 0.01 |
| 53 | 0.0043 |
| 54 | 0.075 |
| 55 | 0.0059 |
| 56 | 0.01 |
| 57 | 0.098 |
| 58 | 0.016 |
| 59 | 0.21 |
| 60 | 0.73 |
| 63 | 0.23 |
| 64 | 0.28 |
| 65 | 0.13 |
| 66 | 0.02 |

We claim:
1. A compound of the formula I

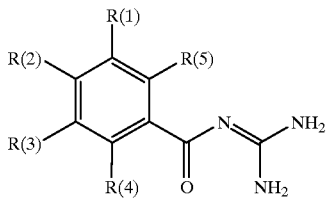

in which:
one of the three substituents R(1), R(2) and R(3) is
R(6)—A—B—D—; wherein
R(6) is a basic protonatable radical selected from the group
consisting of an amino group —NR(7)R(8), an amidino
group R(7)R(8) N—C {=N—R(9)}— and a guanidino
group

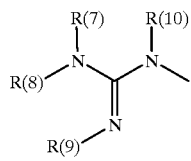

where R(7), R(8), R(9) and R(10) are,
independently of each other, hydrogen or alkyl having 1, 2, 3 or 4 carbon atoms; or
R(7) and R(8) are,
together, $C_aH_{2a}$;
a is 4, 5, 6 or 7;
where, when a=5, 6 or 7, a methylene group of the group $C_aH_{2a}$ can be replaced by a heteroatom group O, $SO_m$ or NR(11), or
R(8) and R(9) or R(9) and R(10) or R(7) and R(10) are a group $C_aH_{2a}$;
a is 2, 3, 4 or 5;
where, when a=3, 4 or 5, a methylene group of the group $C_aH_{2a}$ can be replaced by a heteroatom group O, $SO_m$ or NR(11);
m is zero, 1 or 2;
R(11) is hydrogen or methyl; or
R(6) is a basic heteroaromatic ring system having 1–9 carbon atoms;
A is $C_bH_{2b}$; wherein
b is 1, 2, 3, 4, 5, 6, 7, 8, 9 or 10;
where, in the group $C_bH_{2b}$, one or two methylene groups can be replaced by one of the groups selected from the group consisting of —O—, —CO—, —CH{OR(20)}—, $SO_m$—, —NR(20)—, —NR(20) —CO—, —NR(20)—CO—NH—, —NR(20)—CO—NH—$SO_2$—

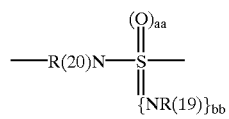

and —$SO_{aa}${NR(10)}$_{bb}$—;
and where, in the group $C_bH_{2b}$, a methylene group can be replaced by —CH—R(99), where R(99), together with R(7), forms a pyrrolidine or piperidine ring;

aa is 1 or 2;
bb is 0 or 1;
aa+bb=2;
R(19) is hydrogen or alkyl having 1, 2, 3 or 4 carbon atoms;
R(20) is a hydrogen or methyl;
B is a phenylene or naphthylene radical

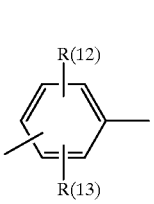 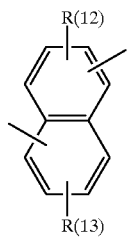

R(12) and R(13) are,
independently of each other, hydrogen, methyl, F, Cl, Br, I, $CF_3$, or —$SO_w$—R(14);
R(14) is methyl or NR(15)R(16);
R(15) and R(16) are,
independently of each other, hydrogen or alkyl having 1, 2, 3 or 4 carbon atoms;
w is zero, 1 or 2;
D is —$C_dH_{2d}$—$X_f$—; wherein
d is zero, 1, 2, 3 or 4;
X is —O—, —CO—, —CH{OR(21)}—, —$SO_m$— or —NR(21)—;
f is 1;
R(21) is hydrogen or methyl;
m is zero, 1 or 2;
and in each case the other two of the substituents R(1) and R(2) and R(3) are,
independently of each other, hydrogen, F, Cl, Br, I, —CN, —($C_1$-$C_8$)-alkyl, —($C_2$-$C_8$)-alkenyl, —NR(35)R(36) or R(17) —$C_gH_{2g}$—$Z_h$—;
g is zero, 1, 2, 3 or 4;
h is zero or 1;
R(35) and R(36) are,
independently of each other, hydrogen or alkyl having 1, 2, 3, 4, 5 or 6 carbon atoms; or
R(35) and R(36) are, together, 4–7 methylene groups in which one $CH_2$ group can be replaced by oxygen, —S—, —NH—, —$NCH_3$ or —N-benzyl;
Z is —O—, —CO—, —$SO_v$—, —NR(18)—, —NR(18)—CO—, —NR(18)—CO—NH— or —NR(18)—$SO_2$—;
R(18) is hydrogen or methyl;
v is zero, 1 or 2;
R(17) is hydrogen, cycloalkyl having 3, 5 or 6 carbon atoms, or $C_kF_{2k+1}$—;
k is 1, 2 or 3, or
R(17) is pyrrol-1-yl, pyrrol-2-yl or pyrrol-3-yl
which is not substituted or is substituted by 1–4 substituents selected from the group consisting of F, Cl, Br, I, —CN, ($C_2$-$C_8$)-alkanoyl, ($C_2$-$C_8$)-alkoxycarbonyl, formyl, carboxyl, —$CF_3$, methyl and methoxy; or
R(17) is —($C_3$-$C_8$)-cycloalkyl or phenyl,
which is not substituted or is substituted by 1–3 substituents selected from the group consisting of F, Cl, —$CF_3$, methyl, hydroxyl, methoxy, —NR(37)R(38), $CH_3SO_2$— and $H_2NO_2S$—;

R(37) and R(38) are independently of each other, hydrogen or —CH$_3$;

R(4) and R(5) are,
independently of each other, hydrogen, alkyl having 1, 2, 3 or 4 carbon atoms, F, Cl, —OR(32), —NR(33)R(34) or —C$_r$F$_{2r+1}$;

R(32), R(33) and R(34) are,
independently of each other, hydrogen or alkyl having 1, 2 or 3 carbon atoms;

r is 1, 2, 3 or 4;
and the pharmacologically tolerated salts thereof.

2. A compound of the formula I as claimed in claim 1, wherein:

R(1) is hydrogen, F, Cl, —(C$_1$–C$_4$)-alkyl, —(C$_2$–C$_4$)-alkenyl, —NR(35)R(36) or R(17)—C$_g$H$_{2g}$—Z$_h$—;

R(35) and R(36) are,
independently of each other, hydrogen, methyl or ethyl; or

R(35) and R(36) are,
together, 4–5 methylene groups in which one CH$_2$group can be replaced by oxygen, —S—, —NH— or —NCH$_3$;

R(17) is hydrogen, cycloalkyl having 5 or 6 carbon atoms, or C$_k$F$_{2k+1}$—;

k is 1, 2 or 3, g is zero, 1, 2, 3 or 4;

h is zero or 1;

Z is —O—, —CO—, —SO$_v$—, —NR(18)—, —NR(18)—CO—, —NR(18)—CO—NH— or —NR(18)—SO$_2$—;

R(18) is hydrogen or methyl;

v is zero, 1 or 2;

or, if g and h are zero,

R(17) is pyrrol-1-yl, pyrrol-2-yl or pyrrol-3-yl, which is not substituted or is substituted by 1–2 substituents selected from the group consisting of F, Cl, (C$_2$–C$_5$)-alkanoyl, (C$_2$–C$_5$)-alkoxy-carbonyl, formyl, carboxyl, —CF$_3$, methyl and methoxy; or R(17) is —(C$_3$–C$_8$)-cycloalkyl or phenyl,
which is not substituted or is substituted by 1–2 substituents selected from the group consisting of F, Cl, —CF$_3$, methyl, methoxy, —NR(37)R(38), CH$_3$SO$_2$— and H$_2$NO$_2$S—;

R(37) and R(38) are,
independently of each other, hydrogen or —CH$_3$;

one of the substituents R(2) and R(3) is R(6)—A—B—D; wherein

R(6) is —NR(7)R(8), an amidino group R(7)R(8)N—C{=N—R(9)}— or a guanidino group

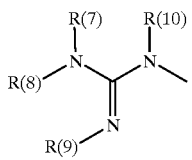

R(7), R(8), R(9) and R(10) are independently of each other, hydrogen or alkyl having 1, 2, 3 or 4 carbon atoms; or R(7) and R(8) are,
together, C$_a$H$_{2a}$;
a is 4, 5, 6 or 7;

where, when a 5, 6 or 7, a methylene group of the group C$_a$H$_{2a}$ can be replaced by a heteroatom group O, SO$_m$ or NR(11);

R(11) is hydrogen or methyl; or

R(8) and R(9) are,
together, C$_a$H$_{2a}$;
a is 2, 3, 4 or 5;
where, when a=3, 4 or 5, a methylene group of the group C$_a$H$_{2a}$ can be replaced by a heteroatom group O, SO$_m$ or NR(11);
m is zero, 1 or 2; or R(6) is imidazolyl, pyridyl, quinolinyl or isoquinolinyl;

A is C$_b$H$_{2b}$;

b is 1, 2, 3, 4 or 5,
where, in the group C$_b$H$_{2b}$, one or two methylene groups can be replaced by one of the groups selected from the group consisting of —O—, —CO—, —CH{OR(20)}—, —SO$_m$—, NR(20), —NR(20), —CO—, —NR(20)—CO—NH—, —NR(20)—CO—NH—SO$_2$—,

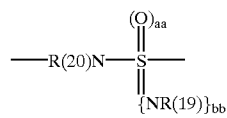

and —SO$_{aa}${NR(19)}$_{bb}$—;

and where, in the group C$_b$H$_{2b}$, a methylene group can be replaced by —CH—R(99), where R(99), together with R(7), forms a pyrrolidine or piperidine ring;

aa is 1 or 2;

bb is 0 or 1;

aa+bb=2;

R(19) is hydrogen or alkyl having 1, 2, 3 or 4 carbon atoms R(20) is hydrogen or methyl;

B is a phenylene or naphthylene radical

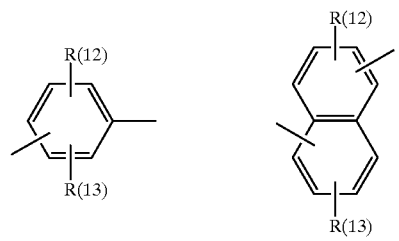

R(12) and R(13) are, independently of each other, hydrogen, methyl, F, Cl, CF$_3$ or —SO$_2$—R(14); R(14) is methyl or NR(15)R(16); R(15) and R(16) are,
independently of each other, hydrogen or alkyl having 1, 2, 3 or 4 carbon atoms;

D is —C$_d$H$_{2d}$—X$_f$; wherein d is zero, 1, 2, 3 or 4;

X is —O—, —CO—, —CH{OR(21)}—, —SO$_m$— or —NR(21)—;

f is 1;

R(21) is hydrogen or methyl;

m is zero, 1 or 2;

and in each case the other of the substituents R(2) and R(3) is hydrogen, alkyl having 1, 2, 3 or 4 carbon atoms, F, Cl or CF$_3$;

R(4) and R(5) are, independently of each other hydrogen, alkyl having 1, 2 or 3 carbon atoms, F, Cl, or —CF$_3$.

3. A compound of the formula I as claimed in claim 1, wherein:

R(1) is hydrogen, F, Cl, alkyl having 1, 2, 3 or 4 carbon atoms, —NR(35)R(36) or R(17)—C$_g$H$_{2g}$—Z$_h$—;
g is zero, 1, 2, 3 or 4;
h is zero or 1;
Z is —O—, —CO—, —SO$_v$—, —NR(18)—, —NR(18)—CO—, —NR(18)—CO—NH— or —NR(18)—SO$_2$—;
R(18) is hydrogen or methyl;
v is zero, 1 or 2;
R(17) is hydrogen, cycloalkyl having 5 or 6 carbon atoms, or CF$_3$—; or, if g and h are zero, R(17) is pyrrol-1-yl,
which is not substituted or is substituted by 1–2 substituents selected from the group consisting of F, Cl, (C$_2$–C$_5$)-alkanoyl, (C$_2$–C$_5$)-alkoxycarbonyl, —CF$_3$ and methyl; or
R(17) is (C$_5$–C$_6$)-cycloalkyl or phenyl,
which is not substituted or is substituted by a substituent which is selected from the group consisting of F, Cl, —CF$_3$, methyl, CH$_3$SO$_2$— and H$_2$NO$_2$S—;
R(35) and R(36) are,
independently of each other, hydrogen, methyl or ethyl; or
R(35) and R(36) are,
together, 4–5 methylene groups in which one CH$_2$ group can be replaced by oxygen, —S—, —NH— or —NCH$_3$;
one of the substituents R(2) and R(3) is
R(6) —A—B—D—; wherein
R(6) is —NR(7)R(8), an amidino group R(7)R(8)N—C{=N—R(9)}— or a guanidino group

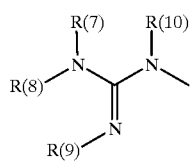

wherein R(7) is
hydrogen or alkyl having 1, 2, 3 or 4 carbon atoms;
R(8), R(9) and R(10) are,
independently of each other, hydrogen, methyl or ethyl; or
R(7) and R(8) are,
together, C$_a$H$_{2a}$;
a is 4 or 5;
where, when a=5, a methylene group of the group C$_a$H$_{2a}$ can be replaced by NR(11),
R(11) is hydrogen or methyl; or
R(6) is imidazolyl or pyridyl;
A is C$_b$H$_{2b}$; wherein
b is 1, 2, 3, 4 or 5,
where, in the group C$_b$H$_{2b}$, one or two methylene groups can be replaced by one of the groups selected from the group consisting of —CO—, —CH{OR(20)}—, —NR(20)—CO—,

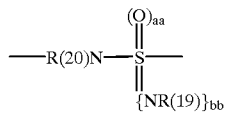

—SO$_{aa}${NR (19)}$_{bb}$ and —SO$_2$—;
and where, in the group C$_{2b}$H$_{2b}$, a methylene group can be replaced by —CH—R(99), where R(99), together with R(7), forms a pyrrolidine or piperidine ring;
aa is 1 or 2;
bb is 0 or 1;
aa+bb=2;
R(19) is hydrogen or alkyl having 1, 2, 3 or 4 carbon atoms R(20) is hydrogen or methyl;
or, if b is 2, 3, 4 or 5,
a carbon atom in C$_b$H$_{2b}$ can be replaced by a grouping ——O—, —S—, —NR(20)—, —NR(20)—CO— or —NR(20)—CO—NH—;
B is a phenylene radical,

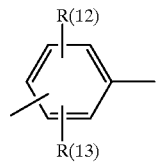

R(12) and R(13) are,
independently of each other, hydrogen, methyl, F, Cl, CF$_3$ or —SO$_2$R(14);
R(14) is methyl or NH$_2$;
D is —CH$_2$—, —O—, —CO—, —SO$_m$— or —NR(21)—;
m is zero or 2;
R(21) is hydrogen or methyl;
and in each case the other of the substituents R(2) and R(3) is
hydrogen;
R(4) and R(5) are,
independently of each other, hydrogen, alkyl having 1, 2 or 3 carbon atoms, F, Cl or —CF$_3$.

4. A compound of the formula I as claimed in claim 1, wherein:

R(1) is hydrogen, F, Cl, alkyl having 1, 2, 3 or 4 carbon atoms, —NR(35)R(36) or R(17)—C$_g$H$_{2g}$—Z$_h$—;
g is zero or 1;
h is zero or 1;
Z is —O—, —CO—, —NR(18)—CO—, —NR(18)—CO—NH— or —NR(18)—SO$_2$—;
R(18) is hydrogen or methyl;
or, if g is 1;
z is —SO$_2$—;
R(17) is hydrogen or CF$_3$—;
R(35) and R(36) are,
independently of each other, hydrogen, methyl or ethyl; or
R(35) and R(36) are,
together, 4–5 methylene groups in which one CH$_2$ group can be replaced by oxygen, —S—, —NH— or —NCH$_3$;

one of the substituents R(2) and R(3) is
R(6) —A—B—O—; wherein
R(6) is —NR(7)R(8) or a guanidino group

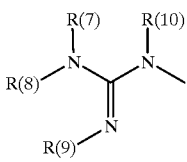

wherein R(7) is
hydrogen or alkyl having 1, 2, 3
or 4 carbon atoms;
R(8), R(9) and R(10) are,
independently of each other, hydrogen, methyl or ethyl;
or
R(7) and R(8) are,
together, $C_aH_{2a}$;
a is 4 or 5;
where, when a=5, a methylene group of the group $C_aH_{2a}$ can be replaced by —NH— or —NCH3—, or
R(6) is imidazolyl;
A is $C_bH_{2b}$; wherein
b is 1, 2, 3 or 4;
where, in the group $C_bH_{2b}$, one or two methylene groups can be replaced by one of the groups selected from the group consisting of —CO—,

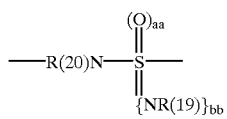

—SO$_{aa}${NR(19)}$_{bb}$— and —SO$_2$—,
and where, in the group $C_bH_{2b}$, a methylene group can be replaced by —CH—R(99), where R(99), together with R(7), can form a pyrrolidine or piperidine ring;
or, if b is 2, 3 or 4,
a methylene group in the group $C_bH_{2b}$ can be replaced by —O— or —S—;
aa is 1 or 2;
bb is 0 or 1;
aa+bb=2;
R(19) is hydrogen or alkyl having 1, 2, 3 or 4 carbon atoms (R20) is hydrogen or methyl;
B is a phenylene radical,

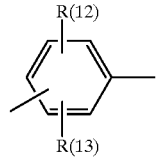

R(12) and R(13) are,
hydrogen;
and in each case the other of the substituents R(2) and R(3) is
hydrogen;
R(4) and R(5) are
hydrogen.

5. A compound of the formula I as claimed in claim 1, which is selected from the group consisting of 4-{4-N-(dimethylaminoethyl)methylsulfamoyl} phenoxy-3-trifluoromethylbenzoylguanidine dihydrochloride; 4-{4-(4-methylpiperazinosulfonyl)phenoxy}-3-trifluoromethylbenzoylguanidine dihydrochloride; 4-{4-(2-pyrrolidineethylaminosulfonyl)phenoxy}-3-trifluoromethylbenzoylguanidine dimaleate; 4-{4-(2-piperidineethylaminosulfonyl)phenoxy}-3-trifluoromethylbenzoylguanidine dimaleate; 4-{4-(N-dimethylamino-n-propyl)sulfamoyl} phenoxy-3-trifluoromethylbenzoylguanidine; 4-{4-(N-dimethylaminoethyl)sulfamoyl}phenoxy-3-trifluoromethylbenzoylguanidine; 4-{4-imidosulfamoyl)phenoxy-3-trifluoromethylbenzoylguanidine; 3-trifluoromethyl-4-(4-N-methylimidosulfamoyl)-phenoxybenzoylguanidine; 3-methyl-4-(4-(1-methylpiperazin-4-ylsulfonyl)-phenoxybenzoylguanidine; 4-(4-guanidinosulfonyl)phenoxy-3-trifluoromethylbenzoylguanidine; 4-{4-(2-imidazolylthioacetyl)phenoxy}-3-methyl-sulfonylbenzoylguanidine dihydrochloride; 4-{4-(N,N'-diimethyl-S-isothiuronylacetyl)phenoxy}-3-methylsulfonylbenzoylguanidine dihydrochloride; 4-{4-(2-benzimidazolylthioacetyl)phenoxy}-3-methyl-sulfonylbenzoylguanidine dihydrochloride; 4-{4-(2-imidazolyl-1-hydroxyethyl)phenoxy}-3-methylsulfonylbenzoylguanidine dihydrochloride; 4-{4-(N,N-dimethylglycylamino)phenoxy}-3-methyl-sulfonylbenzoylguanidine dihydrochloride; 4-{4-(N,N-diethylaminoethyl)aminosulfonylphenoxy}-3-methylsulfonylbenzoylguanidine dihydrochloride; 4-{4-(4-imidazolylethyl)aminosulfonylphenoxy}-3-methylsulfonylbenzoylguanidine dihydrochloride; 4-{4-(3-N-imidazolyl-1-propyl)aminosulfonylphenoxy}-3-methylsulfonylbenzoylguanidine dihydrochloride; 4-{4-(1-methyl-2-pyrrolidinylethyl)aminosulfonylphenoxy}-3-methylsulfonylbenzoylguanidine dihydrochloride; 4-{4-(N-piperidinoethyl)aminosulfonylphenoxy}-3-methylsulfonylbenzoylguanidine dihydrochloride; 4-{4-(2-dimethylaminoethyl)sulfonylmethylphenoxy}-3-methylsulfonylbenzoylguanidine dihydrochloride; 4-{4-(2-dimethylaminoethyl)sulfonylmethylphenoxy}-3-trifluoromethylbenzoylguanidine dihydrochloride.

6. A process for preparing a compound I as claimed in claim 1, which comprises reacting a compound of the formula II

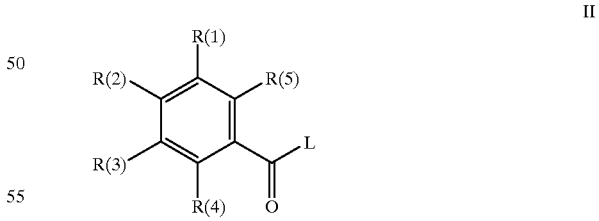

in which R(1) to R(5) are defined as in claim 1 and L is a leaving group which can be substituted nucleophilically, with guanidine.

7. A process for preparing a compound I as claimed in claim 6, further comprising the step of converting compound I into a pharmacologically tolerated salt.

8. A process for preparing a compound I as claimed in claim 6, wherein L is selected from the group consisting of alkoxy, phenoxy, phenylthio, methylthio, 3-pyridyloxy, 2-pyridylthio, a nitrogen heterocycle, Cl, OH, and —OCH$_3$.

9. A method of preparing a medicament for treating arrhythmias comprising using compound I as claimed in claim 1.

10. A method for treating arrhythmias, wherein a composition comprising an effective amount of compound I as claimed in claim 1 is administered in a suitable form for administration.

11. A method for the treatment or prophylaxis of cardiac infarction comprising administering an effective amount of compound I as claimed in claim 1.

12. A method for the treatment or prophylaxis of angina pectoris comprising administering an effective amount of compound I as claimed in claim 1.

13. A method for the treatment or prophylaxis of ischemic conditions of the heart comprising administering an effective amount of compound I as claimed in claim 1.

14. A method for the treatment or prophylaxis of ischemic conditions of the peripheral and central nervous system and of stroke comprising administering an effective amount of compound I as claimed in claim 1.

15. A method for the treatment or prophylaxis of ischemic conditions of peripheral organs and limbs comprising administering an effective amount of compound I as claimed in claim 1.

16. A method for the treatment of shock comprising administering an effective amount of compound I as claimed in claim 1.

17. A method for use in surgical operations and organ transplants comprising administering an effective amount of compound I as claimed in claim 1.

18. A method for the preservation and storage of transplants for surgical procedures comprising administering an effective amount of compound I as claimed in claim 1.

19. A method for the treatment of diseases in which cell proliferation represents a primary or secondary cause, comprising administering an effective amount of compound I as claimed in claim 1 as an antiatherosclerotic agent, or an agent against late complications in diabetes, cancers, pulmonary fibrosis, hepatic fibrosis or renal fibrosis, or prostate hyperplasia.

20. A method for diagnosing hypertension and proliferative diseases comprising administering an effective amount of compound I as claimed in claim 1 as a diagnostic for inhibiting the $Na^+/H^+$ exchanger.

21. A pharmaceutical comprising an effective amount of compound I as claimed in claim 1.

* * * * *